US008076081B2

(12) United States Patent
Kurnit et al.

(10) Patent No.: US 8,076,081 B2
(45) Date of Patent: Dec. 13, 2011

(54) SYSTEMS, METHODS, AND COMPOSITIONS FOR DETECTION OF HUMAN PAPILLOMA VIRUS IN BIOLOGICAL SAMPLES

(75) Inventors: David M. Kurnit, Ann Arbor, MI (US); Michael D. Kane, West Lafayette, IN (US)

(73) Assignee: The Regents of the University of Michigan, Ann Arbor, MI (US)

( * ) Notice: Subject to any disclaimer, the term of this patent is extended or adjusted under 35 U.S.C. 154(b) by 950 days.

(21) Appl. No.: 11/333,738

(22) Filed: Jan. 17, 2006

(65) Prior Publication Data
US 2006/0160188 A1    Jul. 20, 2006

Related U.S. Application Data

(60) Provisional application No. 60/644,374, filed on Jan. 14, 2005.

(51) Int. Cl.
*C12Q 1/68* (2006.01)
*C12P 19/34* (2006.01)

(52) U.S. Cl. ..................... 435/6.12; 435/91.2
(58) Field of Classification Search ............... 435/6.12
See application file for complete search history.

(56) References Cited

U.S. PATENT DOCUMENTS

| 6,368,834 B1 * | 4/2002 | Senapathy et al. ........... 435/91.1 |
| 2006/0160188 A1 | 7/2006 | Kurnit et al. |

FOREIGN PATENT DOCUMENTS

| WO | 94/26934 | 11/1994 |
| WO | 2004/030636 | 4/2004 |

OTHER PUBLICATIONS

Ding et al. PNAS vol. 100:3059-3064. 2003.*
Kan et al. British Journal of Cancer vol. 93:946-948. 2005.*
Serth et al. Nucleic Acids Research vol. 26:4401-4408. 1998.*
Knoth et al. Nucleic Acids Research vol. 16:10932. 1988.*
Capone et al. Clinical Cancer Research vol. 6:4171-4175. 2000.*
Brinkman et al. Journal of Clinical Microbiology vol. 40:3155-3161. 2002.*
DeGaetani et al. Journal of Clinical Pathology vol. 52:103-106. 1999.*
Perrons et al., "Detection and Genotyping of Human Papillomavirus DNA by SPF10 and MY09/11 Primers in Cervical Cells Taken from Women Attending a Colposcopy Clinic" *Journal of Medical Virology* 2002, vol. 67, pp. 246-252, especially pp. 246-248.
Castle et al., "Comparisons of HPV DNA Detection by MY09/11 PCR Methods" *Journal of Medical Virology* 2002, vol. 68, pp. 417-423, especially pp. 417-419.

(Continued)

*Primary Examiner* — Kenneth R. Horlick
(74) *Attorney, Agent, or Firm* — Casimir Jones SC

(57) ABSTRACT

The present invention comprises, without limitation, systems, methods, and compositions for the detection, identification, and quantification, down to the single copy level, of human papillomavirus (HPV) in biological samples, including but not limited to, mammalian body fluids and cervix scrapings, for purposes of detection, treatment and/or management of cancer and dysplasia.

11 Claims, 4 Drawing Sheets

OTHER PUBLICATIONS

Garland et al., "Prevalence of Sexually Transmitted Infections (Neisseria Gonorrhoeae, Chlamydia Trachomatis, Trichomonas Vaginalis and Human PapillomaVirus) in Female Attendees of a Sexually Transmitted Diseases Clinic in Ulaanbaatar, Mongolia," 2001, vol. 9, pp. 143-146, especially pp. 143 and 145.

Fuessel Haws et al., "Nested PCR With the PGMY09/11 and GP5+/6+ Primer Sets Improves Detection of HPV DNA in Cervical Samples", *Journal of Virological Methods* 2004, vol. 122, pp. 87-93, especially pp. 87-90.

PCT International Search Report for PCT/IB06/00063; 4 pages.

Amexis, et al. Quantitative mutant analysis of viral quasispecies by chip-based matrix--assisted laser desorption/ionization time-of-flight mass spectrometry: PNAS, vol. 98, pp. 12097-12102 (2001).

Bosch, et al., Prevalence of Human Papilloma Virus in Cervical Cancer: A Worldwide Perspective. International Biological Study on Cervical Cancer (IBSCC) Study Group. J Natl Cancer Inst, 1995. 87(11)- P. 796-802.

Castle, et al., Restricted Cross-Reactivity of Hybrid Capture 2 With Nononcogenic Human Papillomavirus Types, Cancer Epidemiol Biomarkers Prev, 2002.11(11): p. 1394-9.

Chang, et al. High-Risk Human Papillomaviruses May Have an Important Role in Non-Oral Habitsassociated Oral Squamous Cell Carcinomas in Taiwan. Am J Clin Pathol, 2003.120(6): p. 909-16.

Chin-Hong, et al. Age-Related Prevalence of Anal Cancer Precursors in Homosexual Men: The Explore Study. J Natl Cancer Inst, 2005. 97(12): p. 896-905.

De Roda Husman, et al. The Use of General Primers GP5 and GP6 Elongated A T Their 3' Ends With Adjacent Highl Y Conserved Sequences Improves Human Papillomavirus Detection by PCR, J Gen Virol, 1995.76 (PT 4): p. 1057-62.

Ding, et al. Quantitative Analysis of Nucleic Acids—The Last Few Years of Progress. J Biochem Mol Biol, 2004. 37(1): p. 1-10.

Elvidge, et al., Developmentand Evaluation of Real Competitive PCR for High-Throughput Quantitative Applications. Anal Biochem, 2005.339(2): p. 231-41.

Gillison, et al., Evidence for a Causal Association Between Human Papillomavirus and a Subset of Head and Neck Cancers. J Nail Cancer Inst, 2000. 92(9): p. 709-20.

Gravitt, et al. Genotyping of 27 Human Papilloma Virus Types by Using L 1 Consensus PCR Products BYA Single-Hybridization, Reverse Line Blot Detection Method. J Clin Microbiol, 1998.36(10): p. 3020-7.

Ha, et al., Real-Time Quantitative PCR Demonstrates Low Prevalence of Human Papillomavirus Type 16 in Premalignant and Malignant Lesions of the Oral Cavity. Clin Cancer Res, 2002. 8(5): p. 1203-9.

Heid, et al. Real Time Quantitative PCR, in Genome Research. 1996. p. 986-994.

Herrero, et al., Human Papillomavirus and Oral Cancer: The International Agency for Research on Cancer Multicenter Study. J Natl Cancer Inst, 2003, 95(23): p. 1772-83.

Jacobs, et al., Group-Specific Differentiation Between Highand Low-Risk Human Papillomavirus Genotypes by General Primermediated PCR and Two Cocktails of Oligonucleotide Probes. J Clin Microbiol, 1995.33(4): p. 901-5.

Jurinke, et al. "Application of nested PCR and mass spectrometry for DNA-based virus detection: HBV-DNA detected in the majority of isolated anti-HBc positive sera" Genetic Analysis: Biomolecular Engineering, vol. 14, pp. 97-102 (1998).

Khaled, et al. Human Papilloma Virus Infection and Overexpression of P53 Protein in Bilharzial Bladder Cancer Tumori, 2001. 87(4): p. 256-61.

Koch, et al., Head and Neck Cancer in Nonsmokers: A Distinct Clinical and Molecular Entity. Laryngoscope, 1999. 109(10): p. 1544-51.

McKaig, et al., Human Papillomavirus and Head and Neck Cancer: Epidemiologyand Molecular Biology. Head Neck, 1998. 20(3): p. 250-65.

Moberg, et al. Type-Specific Associations of Human Papillomavirus Load With Risk of Developing Cervical Carcinoma in Situ. Int J Cancer, 2004.112(5): p. 854-9.

Munoz, et al., Epidemiologic Classification of Human Papillomavirus Types Associated With Cervical Cancer. N Engi J Med, 2003.348(6): p. 518-27.

Nam, et al. Nanoparticle-Based Bio-Bar Codes for the Ultrasensitive Detection of Proteins. Science, 2003. 301(5841): p. 1884-6.

Nam, et al., Bio-Bar-Code-Based DNA Detection With PCR-Like Sensitivity. Jam Chem Soc, 2004.126(19): p. 5932-3.

Nelson, et al. A Novel and Rapid PCR-Based Method for Genotyping Human Papillomaviruses in Clinical Samples. J Clin Microbiol, 2000. 38(2): p. 688-95.

Neville, et al. Oral Cancer and Precancerous Lesions. CA Cancer J Clin, 2002. 52(4): p. 195-215.

Obiso, et al. Digene Corporation. Pharmacogenomics, 2004. 5(1): p. 129-32.

Polak, et al., Hybrid Capture /I HPV Test Detects At Least 15 Human Papilloma Virus Genotypes Not Included in Its Current High Risk Probe Cocktail. J Clin Virol, 2002. 25 Suppl 3: p. S89-97.

Rock, et al., Prevention of Cervix Cancer. Crit Rev Oncol Hematol, 2000. 33(3): p. 169-85.

Scheffner, et al., The E6 Oncoprotein Encoded by Human Papillomavirus Types 16 and 18 Promotes the Degradation of P53. Cell, 1990. 63(6): p. 1129-36.

Schwartz, et al., Human Papillomavirus Infection and Survival in Oral Squamous Cell Cancer: A Population-Based Study. Otolaryngol Head Neck Surg, 2001.125(1): p. 1-9.

Schwartz, et al., Oral Cancer Risk in Relation to Sexual History and Evidence of Human Papillomavirus Infection. J Natl Cancer Inst, 1998.90(21): p. 1626-36.

Seybolt, et al. [Exfoliative Cytology: Its Value in the Diagnosis of Cancer.]. Arch Med Cuba, 1953.4(6): p. 579-86.

Sjöholm, et al. "Multiplex Detection of Human Herpesviruses from Archival Specimens by Using Matrix-Assist Laser Desorption Ionization—Time of Flight Mass Spectrometry" J. Clin. Microbiol., vol. 46, pp. 540-5.

Stroun, et al., Isolation and Characterization of DNA From the Plasma of Cancer Patients. Eur J Cancer Clin Oncol, 1987.23(6): p. 707-12.

Tang, et al. Mining Disease Susceptibility Genes Through SNP Analyses and Expression Profiling Using Maldi-Tof Mass Spectrometry. J Proteome Res. 2004.3(2): p. 218-27.

Thompson, et al. Expression of Human Papillomavirus Type 6 E1, E2, L 1 and L2 Open Reading Frames in *Escherichia coli*. Gene, 1987.56(2-3): p. 289-95.

Tost, et al. "Genotyping single nucleotide polymorphisms by MALDI mass spectrometry in clinical applications" Clin. Biochem., vol. 38, pp, 335-50 (2005).

van den Boom, et al. "MALDI-TOF MAS: a platform technology for genetic discovery" Int. J, Mass Spectrometry, vol. 238, pp. 173-86 (2004).

Van Ham, et al., Comparison of Two Commercial Assays for Detection of Human Papillomavirus (HPV) in Cervical Scrape Specimens: Validation of the Roche Amplicor HPV Test As a Means to Screen for HPV Genotypes Associated With a Higher Risk of Cervical Disorders. J Clin Microbiol, 2005. 43(6): p. 2662-7.

Walboomers, et al., Human Papillomavirus is a Necessary Cause of Invasive Cervical Cancer Worldwide. J Pathol, 1999.189(1): p. 12-9.

Widschwendter, et al. "Human Papillomavirus DNA in sera of cervical canceer patients as tumor marker"Cancer Letters, vol. 202, pp. 231-9 (2003).

Yang, et al., Quantification of Human Papillomavirus DNA in the Plasma of Patients With Cervical Cancer. Int J Gynecol Cancer, 2004. 14(5): p. 903-10.

Yang, et al., Sensitive Detection of Human Papillomavirus in Cervical, Head/Neck, and Schistosomiasis-Assoc/ated Bladder Malignancies. Proc Natl Acad Sci USA, 2005.102(21): p. 7683-8.

Lowe, et al. "A computer program for selection of Oligonucleotide primers for polymerase chain reactions" Nucl Acids Res, vol. 18, pp. 1757-61 (1990).

Flores-Munguia, Roberto, et al., "Performance Assessment of Eight High-Throughput PCR Assays for Viral Load Quantitation of Oncogenic HPV types," Journal of Molecular Diagnostics, 2004, vol. 6:115-124.

Forslund, Ola, et al., "A broad range of human papillomavirus types detected with a general PCR method suitable for analysis of cutaneous tumours and normal skin", Journal of General Virology, 1999, 80:2437-2443.

Kinoshita, Moritoshi, et al., "A Sensitive and Quantitative Method for the Determination of Number of HPV16 DNA Copies by Using the Competitive Polymerase Chain Reaction", Elsevier Science Publishing Co., Inc., 1993, 10(5) 116-121.

Capone, Randolph, et al., "Detection and Quantitation of Human Papillomavirus (HPV) DNA in the Sera of Patients with HPV-associated Head and Neck Squamous Cell Carcinoma", Clinical Cancer Research, 2000, vol. 6:4171-4175.

Tseng, Chih-Jen, et al., "Detection of Human Papillomavirus Types 16 and 18 mRNA in Peripheral Blood of Advanced Cervical Cancer Patients and Its Association with Prognosis" Journal of Clinical Oncology, 1999 vol. 17:1391-1396.

Ding, Chunming, et al., "A high-throughput gene expression analysis technique using competitive PCR and matrix-assisted laser desorption ionization time-of-flight MS", PNAS, 2003, vol. 100(6):3059-3064.

Amexis, Georgios, et al., "Quantitative mutant analysis of viral quasispecies by chip-based matrix-assisted laser desorption/ionization time-of-flight mass spectrometry", PNAS, 2001, vol. 98(21):142097-12102.

Abstracts of the General Meeting of the American Society of Microbiology, 2002, vol. 102, pp. 137-138, C-211.

* cited by examiner

SEQUENCE LISTING

```
<160> NUMBER OF SEQ ID NOS: 154

<210> SEQ ID NO 1
<211> LENGTH: 22
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (14)..(14)
<223> OTHER INFORMATION: Inosine

<400> SEQUENCE: 1
tgaaaaacga cganttcaca ac                                              22

<210> SEQ ID NO 2
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (14)..(14)
<223> OTHER INFORMATION: Inosine

<400> SEQUENCE: 2
gtgccagaaa ccantgaacc                                                 20

<210> SEQ ID NO 3
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
```

<223> OTHER INFORMATION: Inosine

<400> SEQUENCE: 3
agaacggcca nacaaattgc                                          20

<210> SEQ ID NO 4
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 4
tgttttgcaa ngggggaactg                                         20

<210> SEQ ID NO 5
<211> LENGTH: 19
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 5
ttaactccgg nggaaaagc                                           19

<210> SEQ ID NO 6
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (12)..(12)
<223> OTHER INFORMATION: Inosine

<400> SEQUENCE: 6
gaccacgtac antgcaccag                                          20

<210> SEQ ID NO 7
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 7
aagggttang accgaaaacg                                          20

<210> SEQ ID NO 8
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)

<223> OTHER INFORMATION: Inosine

<400> SEQUENCE: 8
aaagtggtga nccgaaaacg                                                    20

<210> SEQ ID NO 9
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 9
acatgtcaan aaccgctgtg                                                    20

<210> SEQ ID NO 10
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 10
ggaaaaaccn cgaacattgc                                                    20

<210> SEQ ID NO 11
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (8)..(8)
<223> OTHER INFORMATION: Inosine

<400> SEQUENCE: 11
aggagaancc acggacattg                                                    20

<210> SEQ ID NO 12
<211> LENGTH: 19
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 12
gaggatccng caacacgac                                                     19

<210> SEQ ID NO 13
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)

```
<223> OTHER INFORMATION: Inosine

<400> SEQUENCE: 13
tccactggan aagcaaaagc                                                     20

<210> SEQ ID NO 14
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (7)..(7)
<223> OTHER INFORMATION: Inosine

<400> SEQUENCE: 14
agaacgnccc agaacgctac                                                     20

<210> SEQ ID NO 15
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 15
cggaggaana acaattgcac                                                     20

<210> SEQ ID NO 16
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 16
aatggcgcna tttcacaacc                                                     20

<210> SEQ ID NO 17
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 17
tgcacagagc ngcaaacaac                                                     20

<210> SEQ ID NO 18
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
```

<223> OTHER INFORMATION: Inosine

<400> SEQUENCE: 18
tgcagtcccg ngctattacc                                          20

<210> SEQ ID NO 19
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 19
tggctgtgcn tatgcttctg                                          20

<210> SEQ ID NO 20
<211> LENGTH: 21
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 20
ctagcgaatg nttgtgttgt c                                        21

<210> SEQ ID NO 21
<211> LENGTH: 21
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 21
gttcggattg nagtctgcaa c                                        21

<210> SEQ ID NO 22
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 22
gctaacgcgn gaaattgacc                                          20

<210> SEQ ID NO 23
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (8)..(8)

```
<223> OTHER INFORMATION: Inosine

<400> SEQUENCE: 23
gtttctcngc gtcgttggag                                                   20

<210> SEQ ID NO 24
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 24
acactgcccn cggtactgtc                                                   20

<210> SEQ ID NO 25
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 25
ttgctgtagn ggtcgtctgc                                                   20

<210> SEQ ID NO 26
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 26
tttcagacnc gctgcatacg                                                   20

<210> SEQ ID NO 27
<211> LENGTH: 19
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (6)..(6)
<223> OTHER INFORMATION: Inosine

<400> SEQUENCE: 27
aaacangacc cggtccaac                                                    19

<210> SEQ ID NO 28
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
```

<223> OTHER INFORMATION: Inosine

<400> SEQUENCE: 28
tgccttctng cagaacacac                                          20

<210> SEQ ID NO 29
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 29
ttcgtggtcn ttccctcttg                                          20

<210> SEQ ID NO 30
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (8)..(8)
<223> OTHER INFORMATION: Inosine

<400> SEQUENCE: 30
tgcaattncc gaggtctttc                                          20

<210> SEQ ID NO 31
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 31
ggacatacnc cgacctgtcc                                          20

<210> SEQ ID NO 32
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 32
ttgcattccn cgcactgtag                                          20

<210> SEQ ID NO 33
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)

```
<223> OTHER INFORMATION: Inosine

<400> SEQUENCE: 33
ttttgcattc nacgcatttc                                                     20

<210> SEQ ID NO 34
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 34
tgcagcctna tttcatgcac                                                     20

<210> SEQ ID NO 35
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 35
cagttgcaga nggtctccag                                                     20

<210> SEQ ID NO 36
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 36
cagcccatng taaggtttcc                                                     20

<210> SEQ ID NO 37
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (8)..(8)
<223> OTHER INFORMATION: Inosine

<400> SEQUENCE: 37
ccaacacngc aaacatgacc                                                     20

<210> SEQ ID NO 38
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (7)..(7)
```

<223> OTHER INFORMATION: Inosine

<400> SEQUENCE: 38
acgtcangca atgtggtgtc                                              20

<210> SEQ ID NO 39
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 39
atgcataaan cccgaaaagc                                              20

<210> SEQ ID NO 40
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 40
tcccaaaana caaggccatc                                              20

<210> SEQ ID NO 41
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 41
tttggcctan aggtcgttgc                                              20

<210> SEQ ID NO 42
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 42
cctcagaggn ggtacatgag                                              20

<210> SEQ ID NO 43
<211> LENGTH: 18
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (8)..(8)

```
<223> OTHER INFORMATION: Inosine

<400> SEQUENCE: 43
cgggcggngt gtacaagg                                          18

<210> SEQ ID NO 44
<211> LENGTH: 22
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 44
gaattaatcc ncatcatcca cc                                     22

<210> SEQ ID NO 45
<211> LENGTH: 17
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (7)..(7)
<223> OTHER INFORMATION: Inosine

<400> SEQUENCE: 45
ccgagcncga caggaac                                           17

<210> SEQ ID NO 46
<211> LENGTH: 19
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (8)..(8)
<223> OTHER INFORMATION: Inosine

<400> SEQUENCE: 46
agacaccnta aggacaaac                                         19

<210> SEQ ID NO 47
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 47
ttgcaggaca ntacaatagc                                        20

<210> SEQ ID NO 48
<211> LENGTH: 19
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (6)..(6)
```

<223> OTHER INFORMATION: Inosine

<400> SEQUENCE: 48
ggaacngcaa gaaagagag                                                    19

<210> SEQ ID NO 49
<211> LENGTH: 22
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 49
ggaaagcaan tgcattgtga ca                                                22

<210> SEQ ID NO 50
<211> LENGTH: 21
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (13)..(13)
<223> OTHER INFORMATION: Inosine

<400> SEQUENCE: 50
cattgctgga gcngcaactt g                                                 21

<210> SEQ ID NO 51
<211> LENGTH: 21
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 51
ggtgcatana aaagtgcagt g                                                 21

<210> SEQ ID NO 52
<211> LENGTH: 18
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 52
gtgcaaaccn acagacgc                                                     18

<210> SEQ ID NO 53
<211> LENGTH: 18
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)

```
<223> OTHER INFORMATION: Inosine

<400> SEQUENCE: 53
ccataacanc ggtggacg                                                 18

<210> SEQ ID NO 54
<211> LENGTH: 20
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (7)..(7)
<223> OTHER INFORMATION: Inosine

<400> SEQUENCE: 54
gaacatngca tgatttgtgc                                               20

<210> SEQ ID NO 55
<211> LENGTH: 21
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 55
cattgcatga nttgtgtcag g                                             21

<210> SEQ ID NO 56
<211> LENGTH: 22
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 56
tgtgtgaggn gctggaagaa tc                                            22

<210> SEQ ID NO 57
<211> LENGTH: 25
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (13)..(13)
<223> OTHER INFORMATION: Inosine

<400> SEQUENCE: 57
gaaaaaaaac ggnttcatca aatag                                         25

<210> SEQ ID NO 58
<211> LENGTH: 21
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (8)..(8)
```

<223> OTHER INFORMATION: Inosine

<400> SEQUENCE: 58
agctatgnga aagcttgaat a                     21

<210> SEQ ID NO 59
<211> LENGTH: 23
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (12)..(12)
<223> OTHER INFORMATION: Inosine

<400> SEQUENCE: 59
aggaaaaaca antgcactgt gaa                   23

<210> SEQ ID NO 60
<211> LENGTH: 21
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (9)..(9)
<223> OTHER INFORMATION: Inosine

<400> SEQUENCE: 60
gcgctattnc acaaccctga g                     21

<210> SEQ ID NO 61
<211> LENGTH: 19
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 61
aagcaacagn tactgcgac                        19

<210> SEQ ID NO 62
<211> LENGTH: 22
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (10)..(10)
<223> OTHER INFORMATION: Inosine

<400> SEQUENCE: 62
ccgtgctatn acctgccaaa ag                    22

<210> SEQ ID NO 63
<211> LENGTH: 24
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)

<223> OTHER INFORMATION: Inosine

<400> SEQUENCE: 63
caatttgaaa ntcaacaatt ttat                                          24

<210> SEQ ID NO 64
<211> LENGTH: 23
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (11)..(11)
<223> OTHER INFORMATION: Inosine

<400> SEQUENCE: 64
gcgcaattca ntacctcatt taa                                           23

<210> SEQ ID NO 65
<211> LENGTH: 23
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (13)..(13)
<223> OTHER INFORMATION: Inosine

<400> SEQUENCE: 65
atgaagtcgg aantgctagt aat                                           23

<210> SEQ ID NO 66
<211> LENGTH: 25
<212> TYPE: DNA
<213> ORGANISM: Artificial
<220> FEATURE:
<223> OTHER INFORMATION: DNA Primer
<220> FEATURE:
<221> NAME/KEY: misc_feature
<222> LOCATION: (15)..(15)
<223> OTHER INFORMATION: Inosine

<400> SEQUENCE: 66
cgcaagatta aaacncaaag gaatt                                         25

<210> SEQ ID NO 67
<211> LENGTH: 102
<212> TYPE: DNA
<213> ORGANISM: Artificial
<220> FEATURE:
<223> OTHER INFORMATION: DNA Primer

<400> SEQUENCE: 67
gtttctctgc gtcgttggag tggttcctgt cgtgctcggt tgcagcacga atggcactgg   60
cctctatagt gcccagctat gttgtgaaat cgtcgttttt ca                     102

<210> SEQ ID NO 68
<211> LENGTH: 94
<212> TYPE: DNA
<213> ORGANISM: Artificial
<220> FEATURE:
<223> OTHER INFORMATION: DNA Primer

<400> SEQUENCE: 68
acactgccct cggtactgtc cagctatgct gtgaaatctt ggtttgtcct taaggtgtct   60

```
acgttttcct gctgggttca atggtttctg gcac                                94
```

<210> SEQ ID NO 69
<211> LENGTH: 100
<212> TYPE: DNA
<213> ORGANISM: Artificial
<220> FEATURE:
<223> OTHER INFORMATION: DNA Primer

<400> SEQUENCE: 69

```
ttgctgtagt ggtcgtctgc aatagacaca cgctattgta atgtcctgca aggtggtgtc    60
cagcgttgtg cacaggtctg gcaatttgta tggccgttct                         100
```

<210> SEQ ID NO 70
<211> LENGTH: 104
<212> TYPE: DNA
<213> ORGANISM: Artificial
<220> FEATURE:
<223> OTHER INFORMATION: DNA Primer

<400> SEQUENCE: 70

```
tttcagacac gctgcatacg gtgtacagtc tctatacact ataaataagt cattaaaagc    60
aaattcaaat agctctcttt cttgcagttc ccctttgcaa aaca                    104
```

<210> SEQ ID NO 71
<211> LENGTH: 83
<212> TYPE: DNA
<213> ORGANISM: Artificial
<220> FEATURE:
<223> OTHER INFORMATION: DNA Primer

<400> SEQUENCE: 71

```
aaacatgacc cggtccaacc atgtgctatt agatgaaatc gtcttttgt gtcacaatgc     60 aattgctttt cctccggagt taa                                            83
```

<210> SEQ ID NO 72
<211> LENGTH: 86
<212> TYPE: DNA
<213> ORGANISM: Artificial
<220> FEATURE:
<223> OTHER INFORMATION: DNA Primer

<400> SEQUENCE: 72

```
tgccttcttg cagaacacac aggcaagttg cagctccagc aatggtttat tcacaacttc    60
acatagctgg tgcaatgtac gtggtc                                         86
```

<210> SEQ ID NO 73
<211> LENGTH: 92
<212> TYPE: DNA
<213> ORGANISM: Artificial
<220> FEATURE:
<223> OTHER INFORMATION: DNA Primer

<400> SEQUENCE: 73

```
ttcgtggtct ttccctcttg tcttcgaaca tggtgttctt ctatactttt agcactgcac    60
ttttatatgc accgttttcg gtcataaccc tt                                  92
```

<210> SEQ ID NO 74
<211> LENGTH: 104
<212> TYPE: DNA
<213> ORGANISM: Artificial
<220> FEATURE:
<223> OTHER INFORMATION: DNA Primer -continued
<210> SEQ ID NO 75
<211> LENGTH: 102
<212> TYPE: DNA
<213> ORGANISM: Artificial
<220> FEATURE:
<223> OTHER INFORMATION: DNA Primer

<400> SEQUENCE: 75
ggacatacac cgacctgtcc agcgtccacc gatgttatgg aatcgttttt tttcttctaa    60
atgtctttgc ttttcaactg gacacagcgg tttttgacat gt    102

<210> SEQ ID NO 76
<211> LENGTH: 84
<212> TYPE: DNA
<213> ORGANISM: Artificial
<220> FEATURE:
<223> OTHER INFORMATION: DNA Primer

<400> SEQUENCE: 76
ttgcattcca cgcactgtag ttcaatgttg tgtatagttg tctccaatgc ttcgcacaaa    60
tcatgcaatg ttcgtggttt ttcc    84

<210> SEQ ID NO 77
<211> LENGTH: 87
<212> TYPE: DNA
<213> ORGANISM: Artificial
<220> FEATURE:
<223> OTHER INFORMATION: DNA Primer

<400> SEQUENCE: 77
ttttgcattc aacgcatttc aattcgattt catgcacaga tgtctccaac ccctgacaca    60
aatcatgcaa tgtccgtggt ttctcct    87

<210> SEQ ID NO 78
<211> LENGTH: 80
<212> TYPE: DNA
<213> ORGANISM: Artificial
<220> FEATURE:
<223> OTHER INFORMATION: DNA Primer

<400> SEQUENCE: 78
tgcagcctta tttcatgcac ggattcttcc agcacctcac acaattcgtg cagggtccgg    60
ggtcgtgttg ctggatcctc    80

<210> SEQ ID NO 79
<211> LENGTH: 104
<212> TYPE: DNA
<213> ORGANISM: Artificial
<220> FEATURE:
<223> OTHER INFORMATION: DNA Primer

<400> SEQUENCE: 79
cagttgcaga tggtctccag caccgtgtac agcgtccggt ccactgttct cctatttgat    60
gaaaccgttt ttttcatct acatgctttt gcttttccag tgga    104

<210> SEQ ID NO 80
<211> LENGTH: 104
<212> TYPE: DNA

<400> SEQUENCE: 74
tgcaatttcc gaggtctttc tgcaggattt ttgaacatcg cgtctgtagg tttgcacaaa    60
atactatgtg ctttatatac caaccgtttt cggttcacca cttt    104

<213> ORGANISM: Artificial
<220> FEATURE:
<223> OTHER INFORMATION: DNA Primer

<400> SEQUENCE: 80
cagcccattg taaggtttcc ttgcaatata cacactgtac ctgcaaattt tgcaaagtac    60
tattcaagct ttcacatagc tcatgtagcg ttctgggtcg ttct    104

<210> SEQ ID NO 81
<211> LENGTH: 86
<212> TYPE: DNA
<213> ORGANISM: Artificial
<220> FEATURE:
<223> OTHER INFORMATION: DNA Primer

<400> SEQUENCE: 81
ccaacactgc aaacatgacc cggtccatgc atatgctata taatgaaatc gtcttttatc    60
ttcacagtgc aattgttttt cctccg    86

<210> SEQ ID NO 82
<211> LENGTH: 84
<212> TYPE: DNA
<213> ORGANISM: Artificial
<220> FEATURE:
<223> OTHER INFORMATION: DNA Primer

<400> SEQUENCE: 82
acgtcatgca atgtggtgtc caatgtcctg cacaggtctg gcaatttgta tggccgttgc    60
tcagggttgt gaaatagcgc catt    84

<210> SEQ ID NO 83
<211> LENGTH: 110
<212> TYPE: DNA
<213> ORGANISM: Artificial
<220> FEATURE:
<223> OTHER INFORMATION: DNA Primer

<400> SEQUENCE: 83
atgcataaat cccgaaaagc aaagtcatat acctcaggtc gcagtaactg ttgcttgcag    60
tacacacatt ctaatattat atcatgtata gttgtttgca gctctgtgca    110

<210> SEQ ID NO 84
<211> LENGTH: 85
<212> TYPE: DNA
<213> ORGANISM: Artificial
<220> FEATURE:
<223> OTHER INFORMATION: DNA Primer

<400> SEQUENCE: 84
tcccaaaata caaggccatc ataaggatcc tttttagggg caggggcgga aggacgcttt    60
tggcaggtaa tagcacggga ctgca    85

<210> SEQ ID NO 85
<211> LENGTH: 104
<212> TYPE: DNA
<213> ORGANISM: Artificial
<220> FEATURE:
<223> OTHER INFORMATION: DNA Primer

<400> SEQUENCE: 85
tttggcctat aggtcgttgc tcctcctgct caatttcacg accatacaca gttagctcat    60
aaaattgttg aatttcaaat tgagcagaag cataagcaca gcca    104

<210> SEQ ID NO 86
<211> LENGTH: 107
<212> TYPE: DNA
<213> ORGANISM: Artificial
<220> FEATURE:
<223> OTHER INFORMATION: DNA Primer

<400> SEQUENCE: 86
cctcagagga ggtacatgag acttaaatga ggtaatgaat tgcgcagcca tctgtaaaca    60
tgacgaggct ttgtaaacag aactgggaca acacaaacat tcgctag                107

<210> SEQ ID NO 87
<211> LENGTH: 107
<212> TYPE: DNA
<213> ORGANISM: Artificial
<220> FEATURE:
<223> OTHER INFORMATION: DNA Primer

<400> SEQUENCE: 87
cgggcggtgt gtacaaggcc cgggaacgta ttcacggcgt tatggctgac acgcgattac    60
tagcaattcc gacttcatgt agtcgagttg cagactacaa tccgaac                 107

<210> SEQ ID NO 88
<211> LENGTH: 102
<212> TYPE: DNA
<213> ORGANISM: Artificial
<220> FEATURE:
<223> OTHER INFORMATION: DNA Primer

<400> SEQUENCE: 88
gaattaatcc acatcatcca ccgcttgtgc gggtccccgt gaattccttt gagttttaat    60
cttgcgaccg tactccccag gcggtcaatt tcacgcgtta gc                      102

<210> SEQ ID NO 89
<211> LENGTH: 30
<212> TYPE: DNA
<213> ORGANISM: Artificial
<220> FEATURE:
<223> OTHER INFORMATION: DNA Primer

<400> SEQUENCE: 89
acgttggatg actgcaatgt ttcaggaccc                                     30

<210> SEQ ID NO 90
<211> LENGTH: 30
<212> TYPE: DNA
<213> ORGANISM: Artificial
<220> FEATURE:
<223> OTHER INFORMATION: DNA Primer

<400> SEQUENCE: 90
acgttggatg tagttgtttg cagctctgtg                                     30

<210> SEQ ID NO 91
<211> LENGTH: 19
<212> TYPE: DNA
<213> ORGANISM: Artificial
<220> FEATURE:
<223> OTHER INFORMATION: DNA Primer

<400> SEQUENCE: 91
gagcgaccca gaaagttac                                                 19

<210> SEQ ID NO 92

```
<211> LENGTH: 30
<212> TYPE: DNA
<213> ORGANISM: Artificial
<220> FEATURE:
<223> OTHER INFORMATION: DNA Primer

<400> SEQUENCE: 92
acgttggatg atagctgggc actatagagg                                          30

<210> SEQ ID NO 93
<211> LENGTH: 30
<212> TYPE: DNA
<213> ORGANISM: Artificial
<220> FEATURE:
<223> OTHER INFORMATION: DNA Primer

<400> SEQUENCE: 93
acgttggatg tgtgtttctc tgcgtcgttg                                          30

<210> SEQ ID NO 94
<211> LENGTH: 17
<212> TYPE: DNA
<213> ORGANISM: Artificial
<220> FEATURE:
<223> OTHER INFORMATION: DNA Primer

<400> SEQUENCE: 94
gccattcgtg ctgcaac                                                        17

<210> SEQ ID NO 95
<211> LENGTH: 30
<212> TYPE: DNA
<213> ORGANISM: Artificial
<220> FEATURE:
<223> OTHER INFORMATION: DNA Primer

<400> SEQUENCE: 95
acgttggatg caggattttt gaacatggcg                                          30

<210> SEQ ID NO 96
<211> LENGTH: 30
<212> TYPE: DNA
<213> ORGANISM: Artificial
<220> FEATURE:
<223> OTHER INFORMATION: DNA Primer

<400> SEQUENCE: 96
acgttggatg tggtgaaccg aaaacggttg                                          30

<210> SEQ ID NO 97
<211> LENGTH: 17
<212> TYPE: DNA
<213> ORGANISM: Artificial
<220> FEATURE:
<223> OTHER INFORMATION: DNA Primer

<400> SEQUENCE: 97
atggcgtctg taggttt                                                        17

<210> SEQ ID NO 98
<211> LENGTH: 30
<212> TYPE: DNA
<213> ORGANISM: Artificial
<220> FEATURE:
<223> OTHER INFORMATION: DNA Primer

<400> SEQUENCE: 98
```

```
acgttggatg cacagtgcag tttctctacg                              30

<210> SEQ ID NO 99
<211> LENGTH: 30
<212> TYPE: DNA
<213> ORGANISM: Artificial
<220> FEATURE:
<223> OTHER INFORMATION: DNA Primer

<400> SEQUENCE: 99
acgttggatg cgatttcata atatttcggg                              30

<210> SEQ ID NO 100
<211> LENGTH: 19
<212> TYPE: DNA
<213> ORGANISM: Artificial
<220> FEATURE:
<223> OTHER INFORMATION: DNA Primer

<400> SEQUENCE: 100
acacgccgca cagcgccct                                          19

<210> SEQ ID NO 101
<211> LENGTH: 30
<212> TYPE: DNA
<213> ORGANISM: Artificial
<220> FEATURE:
<223> OTHER INFORMATION: DNA Primer

<400> SEQUENCE: 101
acgttggatg ttccaacagg acatacaccg                              30

<210> SEQ ID NO 102
<211> LENGTH: 30
<212> TYPE: DNA
<213> ORGANISM: Artificial
<220> FEATURE:
<223> OTHER INFORMATION: DNA Primer

<400> SEQUENCE: 102
acgttggatg cgctgtgtcc agttgaaaag                              30

<210> SEQ ID NO 103
<211> LENGTH: 17
<212> TYPE: DNA
<213> ORGANISM: Artificial
<220> FEATURE:
<223> OTHER INFORMATION: DNA Primer

<400> SEQUENCE: 103
acctgtccac cgtccac                                            17

<210> SEQ ID NO 104
<211> LENGTH: 30
<212> TYPE: DNA
<213> ORGANISM: Artificial
<220> FEATURE:
<223> OTHER INFORMATION: DNA Primer

<400> SEQUENCE: 104
acgttggatg gccatacaaa ttgccagacc                              30

<210> SEQ ID NO 105
<211> LENGTH: 30
<212> TYPE: DNA
<213> ORGANISM: Artificial
<220> FEATURE:
```

<223> OTHER INFORMATION: DNA Primer

<400> SEQUENCE: 105
acgttggatg tcgtctgcaa tagacacagg                               30

<210> SEQ ID NO 106
<211> LENGTH: 20
<212> TYPE: DNA
<213> ORGANISM: Artificial
<220> FEATURE:
<223> OTHER INFORMATION: DNA Primer

<400> SEQUENCE: 106
ttgccagacc tgtgcacaac                                          20

<210> SEQ ID NO 107
<211> LENGTH: 30
<212> TYPE: DNA
<213> ORGANISM: Artificial
<220> FEATURE:
<223> OTHER INFORMATION: DNA Primer

<400> SEQUENCE: 107
acgttggatg ctgtgcacaa atctggtagc                               30

<210> SEQ ID NO 108
<211> LENGTH: 30
<212> TYPE: DNA
<213> ORGANISM: Artificial
<220> FEATURE:
<223> OTHER INFORMATION: DNA Primer

<400> SEQUENCE: 108
acgttggatg aagtgcatta caggatggcg                               30

<210> SEQ ID NO 109
<211> LENGTH: 25
<212> TYPE: DNA
<213> ORGANISM: Artificial
<220> FEATURE:
<223> OTHER INFORMATION: DNA Primer

<400> SEQUENCE: 109
aaatctggta gcttgtaggg tcgtt                                    25

<210> SEQ ID NO 110
<211> LENGTH: 30
<212> TYPE: DNA
<213> ORGANISM: Artificial
<220> FEATURE:
<223> OTHER INFORMATION: DNA Primer

<400> SEQUENCE: 110
acgttggatg ggttatgacc gaaaacggtg                               30

<210> SEQ ID NO 111
<211> LENGTH: 30
<212> TYPE: DNA
<213> ORGANISM: Artificial
<220> FEATURE:
<223> OTHER INFORMATION: DNA Primer

<400> SEQUENCE: 111
acgttggatg gtctttccct cttgtcttcg                               30

<210> SEQ ID NO 112

```
<211> LENGTH: 22
<212> TYPE: DNA
<213> ORGANISM: Artificial
<220> FEATURE:
<223> OTHER INFORMATION: DNA Primer

<400> SEQUENCE: 112
cggtgcatat aaaagtgcag tg                                          22

<210> SEQ ID NO 113
<211> LENGTH: 30
<212> TYPE: DNA
<213> ORGANISM: Artificial
<220> FEATURE:
<223> OTHER INFORMATION: DNA Primer

<400> SEQUENCE: 113
acgttggatg attgtgtgag gtgctggaag                                  30

<210> SEQ ID NO 114
<211> LENGTH: 30
<212> TYPE: DNA
<213> ORGANISM: Artificial
<220> FEATURE:
<223> OTHER INFORMATION: DNA Primer

<400> SEQUENCE: 114
acgttggatg acctctcttc gttgtagctc                                  30

<210> SEQ ID NO 115
<211> LENGTH: 18
<212> TYPE: DNA
<213> ORGANISM: Artificial
<220> FEATURE:
<223> OTHER INFORMATION: DNA Primer

<400> SEQUENCE: 115
gtgctggaag aatcggtg                                               18

<210> SEQ ID NO 116
<211> LENGTH: 30
<212> TYPE: DNA
<213> ORGANISM: Artificial
<220> FEATURE:
<223> OTHER INFORMATION: DNA Primer

<400> SEQUENCE: 116
acgttggatg caaacatgac ccggtccaac                                  30

<210> SEQ ID NO 117
<211> LENGTH: 30
<212> TYPE: DNA
<213> ORGANISM: Artificial
<220> FEATURE:
<223> OTHER INFORMATION: DNA Primer

<400> SEQUENCE: 117
acgttggatg gttaactccg gaggaaaagc                                  30

<210> SEQ ID NO 118
<211> LENGTH: 24
<212> TYPE: DNA
<213> ORGANISM: Artificial
<220> FEATURE:
<223> OTHER INFORMATION: DNA Primer

<400> SEQUENCE: 118
```
caaccatgtg ctattagatg aaat                                          24

<210> SEQ ID NO 119
<211> LENGTH: 30
<212> TYPE: DNA
<213> ORGANISM: Artificial
<220> FEATURE:
<223> OTHER INFORMATION: DNA Primer

<400> SEQUENCE: 119
acgttggatg tgatttgtgt caggcgttgg                                    30

<210> SEQ ID NO 120
<211> LENGTH: 30
<212> TYPE: DNA
<213> ORGANISM: Artificial
<220> FEATURE:
<223> OTHER INFORMATION: DNA Primer

<400> SEQUENCE: 120
acgttggatg tacctcagat cgctgcaaag                                    30

<210> SEQ ID NO 121
<211> LENGTH: 20
<212> TYPE: DNA
<213> ORGANISM: Artificial
<220> FEATURE:
<223> OTHER INFORMATION: DNA Primer

<400> SEQUENCE: 121
gtgtcaggcg ttggagacat                                               20

<210> SEQ ID NO 122
<211> LENGTH: 30
<212> TYPE: DNA
<213> ORGANISM: Artificial
<220> FEATURE:
<223> OTHER INFORMATION: DNA Primer

<400> SEQUENCE: 122
acgttggatg gcagttcccc tttgcaaaac                                    30

<210> SEQ ID NO 123
<211> LENGTH: 30
<212> TYPE: DNA
<213> ORGANISM: Artificial
<220> FEATURE:
<223> OTHER INFORMATION: DNA Primer

<400> SEQUENCE: 123
acgttggatg ctgcctgatt tgagcacaac                                    30

<210> SEQ ID NO 124
<211> LENGTH: 21
<212> TYPE: DNA
<213> ORGANISM: Artificial
<220> FEATURE:
<223> OTHER INFORMATION: DNA Primer

<400> SEQUENCE: 124
ttgcaaaaca cacaattgat g                                             21

<210> SEQ ID NO 125
<211> LENGTH: 30
<212> TYPE: DNA
<213> ORGANISM: Artificial
<220> FEATURE:

```
<223> OTHER INFORMATION: DNA Primer

<400> SEQUENCE: 125
acgttggatg accccgtccc tatatactac                              30

<210> SEQ ID NO 126
<211> LENGTH: 30
<212> TYPE: DNA
<213> ORGANISM: Artificial
<220> FEATURE:
<223> OTHER INFORMATION: DNA Primer

<400> SEQUENCE: 126
acgttggatg tgcagaaggc aactacaacg                              30

<210> SEQ ID NO 127
<211> LENGTH: 23
<212> TYPE: DNA
<213> ORGANISM: Artificial
<220> FEATURE:
<223> OTHER INFORMATION: DNA Primer

<400> SEQUENCE: 127
ccctatatac tacatttaag tca                                     23

<210> SEQ ID NO 128
<211> LENGTH: 27
<212> TYPE: DNA
<213> ORGANISM: Artificial
<220> FEATURE:
<223> OTHER INFORMATION: DNA Primer

<400> SEQUENCE: 128
accttctctt gacctttcag aatatgt                                 27

<210> SEQ ID NO 129
<211> LENGTH: 21
<212> TYPE: DNA
<213> ORGANISM: Artificial
<220> FEATURE:
<223> OTHER INFORMATION: DNA Primer

<400> SEQUENCE: 129
agagagtctt ggccctttcc a                                       21

<210> SEQ ID NO 130
<211> LENGTH: 21
<212> TYPE: DNA
<213> ORGANISM: Artificial
<220> FEATURE:
<223> OTHER INFORMATION: DNA Primer

<400> SEQUENCE: 130
agagggccct ctgcctgctg c                                       21

<210> SEQ ID NO 131
<211> LENGTH: 18
<212> TYPE: DNA
<213> ORGANISM: Artificial
<220> FEATURE:
<223> OTHER INFORMATION: DNA Primer

<400> SEQUENCE: 131
gcacagggac ataataat                                           18

<210> SEQ ID NO 132
```

```
<211> LENGTH: 18
<212> TYPE: DNA
<213> ORGANISM: Artificial
<220> FEATURE:
<223> OTHER INFORMATION: DNA Primer

<400> SEQUENCE: 132
gcacagggtc ataataat                                                18

<210> SEQ ID NO 133
<211> LENGTH: 15
<212> TYPE: DNA
<213> ORGANISM: Artificial
<220> FEATURE:
<223> OTHER INFORMATION: DNA Primer

<400> SEQUENCE: 133
gcccagggac ataat                                                   15

<210> SEQ ID NO 134
<211> LENGTH: 15
<212> TYPE: DNA
<213> ORGANISM: Artificial
<220> FEATURE:
<223> OTHER INFORMATION: DNA Primer

<400> SEQUENCE: 134
gcccagggtc ataat                                                   15

<210> SEQ ID NO 135
<211> LENGTH: 25
<212> TYPE: DNA
<213> ORGANISM: Artificial
<220> FEATURE:
<223> OTHER INFORMATION: DNA Primer

<400> SEQUENCE: 135
gaatatgatt tacagtttat ttttc                                        25

<210> SEQ ID NO 136
<211> LENGTH: 25
<212> TYPE: DNA
<213> ORGANISM: Artificial
<220> FEATURE:
<223> OTHER INFORMATION: DAN Primer

<400> SEQUENCE: 136
ctgttgttga tactacacgc agtac                                        25

<210> SEQ ID NO 137
<211> LENGTH: 22
<212> TYPE: DNA
<213> ORGANISM: Artificial
<220> FEATURE:
<223> OTHER INFORMATION: DNA Primer

<400> SEQUENCE: 137
gtggtagata ccacacgcag ta                                           22

<210> SEQ ID NO 138
<211> LENGTH: 22
<212> TYPE: DNA
<213> ORGANISM: Artificial
<220> FEATURE:
<223> OTHER INFORMATION: DNA Primer

<400> SEQUENCE: 138
```

```
gtggtagata ccactcgcag ta                                               22

<210> SEQ ID NO 139
<211> LENGTH: 27
<212> TYPE: DNA
<213> ORGANISM: Artificial
<220> FEATURE:
<223> OTHER INFORMATION: DNA Primer

<400> SEQUENCE: 139
accttctctt gacctttcag aatatgt                                          27

<210> SEQ ID NO 140
<211> LENGTH: 21
<212> TYPE: DNA
<213> ORGANISM: Artificial
<220> FEATURE:
<223> OTHER INFORMATION: DNA Primer

<400> SEQUENCE: 140
agagagtctt ggccctttcc a                                                21

<210> SEQ ID NO 141
<211> LENGTH: 21
<212> TYPE: DNA
<213> ORGANISM: Artificial
<220> FEATURE:
<223> OTHER INFORMATION: DNA Primer

<400> SEQUENCE: 141
agagggccct ctgcctgctg c                                                21

<210> SEQ ID NO 142
<211> LENGTH: 73
<212> TYPE: DNA
<213> ORGANISM: Artificial
<220> FEATURE:
<223> OTHER INFORMATION: DNA Primer

<400> SEQUENCE: 142
tagttgtttg cagctctgtg cataactgtc gtaactttct gggtcgctcc tgtgggtcct      60
gaaacattgc agt                                                        73

<210> SEQ ID NO 143
<211> LENGTH: 83
<212> TYPE: DNA
<213> ORGANISM: Artificial
<220> FEATURE:
<223> OTHER INFORMATION: DNA Primer

<400> SEQUENCE: 143
tgtgtttctc tgcgtcgttg gagtcgttcc tgtcgtgctc cgttgcagca cgaatggcac      60
tggcctctat agtgcccagc tat                                             83

<210> SEQ ID NO 144
<211> LENGTH: 78
<212> TYPE: DNA
<213> ORGANISM: Artificial
<220> FEATURE:
<223> OTHER INFORMATION: DNA Primer

<400> SEQUENCE: 144
caggattttt gaacatggcg tctgtaggtt tccacaaaat actatgtgct ttatatacca      60
accgttttcg gttcacca                                                   78
```

```
<210> SEQ ID NO 145
<211> LENGTH: 81
<212> TYPE: DNA
<213> ORGANISM: Artificial
<220> FEATURE:
<223> OTHER INFORMATION: DNA Primer

<400> SEQUENCE: 145
tcacagtgca gtttctctac gtcgggacct ccaacacgcc gcacagcgcc ctccccaacg      60
acccgaaata ttatgaaatc g                                               81

<210> SEQ ID NO 146
<211> LENGTH: 97
<212> TYPE: DNA
<213> ORGANISM: Artificial
<220> FEATURE:
<223> OTHER INFORMATION: DNA Primer

<400> SEQUENCE: 146
ttccaacagg acatacaccg acctgtccac cgtccacgga tgttatggaa tcgttttttt      60
tcttctaaat gtctttgctt ttcaactgga cacagcg                              97

<210> SEQ ID NO 147
<211> LENGTH: 82
<212> TYPE: DNA
<213> ORGANISM: Artificial
<220> FEATURE:
<223> OTHER INFORMATION: DNA Primer

<400> SEQUENCE: 147
tcgtctgcaa tagacacagg ctattgtaat gtcctgcaag gtggtgtcca gggttgtgca      60
caggtctggc aatttgtatg gc                                              82

<210> SEQ ID NO 148
<211> LENGTH: 84
<212> TYPE: DNA
<213> ORGANISM: Artificial
<220> FEATURE:
<223> OTHER INFORMATION: DNA Primer

<400> SEQUENCE: 148
catgtattac actgccctcg gtactgtcca cctatgctgt gaaatcttcg tttgtcctta      60
aggtgtctac gtttttctgc tggg                                            84

<210> SEQ ID NO 149
<211> LENGTH: 83
<212> TYPE: DNA
<213> ORGANISM: Artificial
<220> FEATURE:
<223> OTHER INFORMATION: DNA Primer

<400> SEQUENCE: 149
gtctttccct cttgtcttcg aacatggtgt tcttctatac ttttagcact gcacttttat      60
atgcaccgtt ttcggtcata acc                                             83

<210> SEQ ID NO 150
<211> LENGTH: 84
<212> TYPE: DNA
<213> ORGANISM: Artificial
<220> FEATURE:
<223> OTHER INFORMATION: DNA Primer

<400> SEQUENCE: 150
```

```
acctctcttc gttgtagctc tttttttgcac tgcacacact gcagccttat ttcatccacc    60
gattcttcca gcacctcaca caat                                            84

<210> SEQ ID NO 151
<211> LENGTH: 85
<212> TYPE: DNA
<213> ORGANISM: Artificial
<220> FEATURE:
<223> OTHER INFORMATION: DNA Primer

<400> SEQUENCE: 151
caaacatgac ccggtccaac catgtgctat tagatgaaat ggtcttttc tgtcacaatg      60 caattgcttt cctccggag ttaac                                            85

<210> SEQ ID NO 152
<211> LENGTH: 88
<212> TYPE: DNA
<213> ORGANISM: Artificial
<220> FEATURE:
<223> OTHER INFORMATION: DNA Primer

<400> SEQUENCE: 152
tacctcagat cgctgcaaag tcttttttgca ttcaacgcat ttcaattcga tttcatgcac    60
acatgtctcc aacgcctgac acaaatca                                        88

<210> SEQ ID NO 153
<211> LENGTH: 79
<212> TYPE: DNA
<213> ORGANISM: Artificial
<220> FEATURE:
<223> OTHER INFORMATION: DNA Primer

<400> SEQUENCE: 153
gcagttcccc tttgcaaaac acacaattga tgggaatatc atgcagagga atattcaatg     60
ttgtgctcaa atcaggcag                                                  79

<210> SEQ ID NO 154
<211> LENGTH: 77
<212> TYPE: DNA
<213> ORGANISM: Artificial
<220> FEATURE:
<223> OTHER INFORMATION: DNA Primer

<400> SEQUENCE: 154
accccgtccc tatatactac atttaagtca gcaaaggcaa attcatatac ctctgtccgt     60
tgtagttgcc ttctgca                                                    77
```

SYSTEMS, METHODS, AND COMPOSITIONS FOR DETECTION OF HUMAN PAPILLOMA VIRUS IN BIOLOGICAL SAMPLES

CROSS-REFERENCE TO RELATED APPLICATIONS

This application claims priority based on U.S. Provisional Patent Application No. 60/644,374, filed Jan. 14, 2005, which is hereby incorporated by reference in full.

GRANT INFORMATION

Work underlying the invention was supported in part by grants from the Michigan Life Sciences Corridor (MEDC-410), the Michigan Tri-Technology Corridor, NIH (R21 DK69877, R21 DK070237, CA104830 and CA94328), the NIH Head/Neck Cancer SPORE (1 P50 CA97248), and the MDRTC Cell and Molecular Biology Core (DK20572). The government may have certain rights in the invention.

FIELD OF THE INVENTION

The present invention relates to the field of detection and management of microbial agents in biological samples.

BACKGROUND

Recent studies indicate that the human papillomavirus ("HPV") is associated with a significant fraction of cervical, head/neck, anal, and schistosomiasis-associated bladder cancers. Cervical and anal cancers are almost uniformly associated with HPV infection. A recent review of published reports found the overall prevalence of HPV DNA in head and neck tumors to be 35%. More recently some researchers have used quantitative PCR ("QPCR") to confirm these findings in a large study of 253 tumor samples, where they detected HPV DNA in 25% of specimens. HPV is also associated with anal dysplasias and cancers. Other researchers have found that nearly 50% of schistosomiasis-caused bladder cancers had HPV DNA by in situ hybridization.

HPV types 16 and 18 are among the 'high risk' viral types since their presence is associated with preneoplastic lesions and carcinomas. In contrast, the 'low risk' types, most commonly HPV types 6 and 11, are typically associated with benign lesions. The oncogenic potential of HPV is principally due to two viral oncoproteins, E6 and E7. Differences in oncogenic potential among HPV types have been attributed to type-specific differences in the E6 and E7 proteins. The E6 protein of oncogenic HPV strains has been shown to interact with the p53 protein and promote its degradation via a ubiquitin-dependent pathway. The E7 oncoprotein can, similarly, complex with the retinoblastoma (Rb) protein and inactivate it. Both p53 and Rb are important tumor suppressor genes whose products regulate the cell cycle, orchestrate DNA repair processes, and are involved with programmed cell death or apoptosis. Disruption of these tumor suppressor proteins by HPV leads to propagation of mutational changes and cell immortalization.

The technique of examining serum DNA for abnormal genomes of cancer cells has been studied as a potential molecular test for cancer. Although some researchers found that the TaqMan quantitative PCR method could detect HPV DNA in serum from some patients with head/neck and cervical cancers, HPV DNA was not detectable by this technique in serum and other biological locations in sufficient amounts to be useful in most subjects as a clinical tool.

As examples of current limitations, problems with the current standard of care for HPV testing, the Digene test [1], include:

1. The Digene test cross-reacts non-specifically with HPV types other than the known pathogenic types [2]. Thus there are unavoidable false positives with the Digene test;

2. The Digene test requires at least several thousand HPV molecules to read as positive [1]. This requirement prevents screening of serum and/or blood where a smaller number of molecules are present; and 3. The Digene test does not reveal which HPV type is found in the cervix ThinPrep. This becomes important as non-pathogenic types of HPV can yield false positive results if the types of HPV responsible for a signal are not identified.

In view of these and other limitations and shortcomings in the art, an unmet need remains for systems, methods, and compositions for the detection and identification of individual HPV species in biological samples at levels not detectable by currently available methods.

SUMMARY OF THE INVENTION

The present invention comprises, without limitation, systems, methods, and compositions for the detection, identification, and quantification, down to the single copy level, of HPV in biological samples, including without limitation, in mammalian bodily fluids and cervix scrapings for purposes of detection, treatment and/or management of cancer and dysplasia. In some preferred embodiments, the invention comprises more sensitive mass spectroscopy technology that identifies individual HPV sequences, increases the sensitivity of detection of HPV DNA, and provides evidence for a more frequent association of serum and/or peripheral-blood HPV-DNA with several tumor types. Thus, the invention comprises systems, methods, and compositions that permit screening of peripheral blood and serum for HPV DNA as a marker of residual tumor or dysplasia in cases associated with HPV.

Other aspects of the invention will be apparent to those skilled in the art after reviewing the drawings and the detailed description below.

DRAWINGS

The present invention will now be described, by way of example, with reference to the accompanying drawings, in which.

Figure 1:
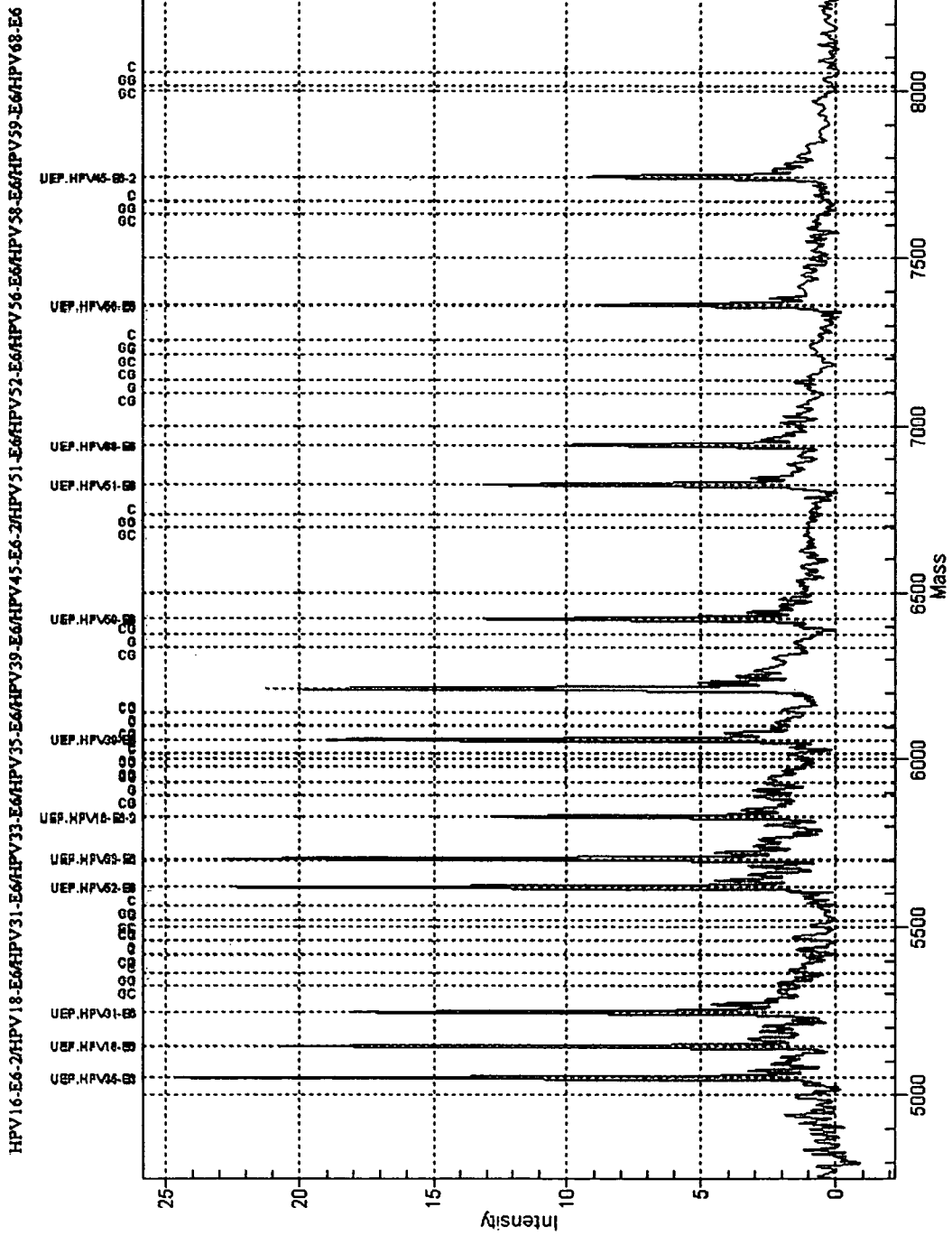
FIG. 1 represents mass spectroscopy results of a screen for thirteen (13) different HPV types in a single reaction in accordance with the invention.

FIGS. 3A-D show HPV titers in tumors (3A), Pap-positive specimens (3B), HC2-positive specimens (3C), and Pap-negative specimens (3D), respectively.

DETAILED DESCRIPTION

Without limitation, in some embodiments, the present invention comprises systems, methods, and compositions to simultaneously analyze and determine which of one or more types of pathogenic HPV is associated with cancer or dysplasia from tumor or dysplastic tissue. Using the invention, this analysis and determination can be done down to the 100 or fewer HPV copy number, which is more sensitive than tests currently approved by the U.S. Food and Drug Administration ("FDA") for HPV detection, which require 1000-5000 copies. [1]. The invention further extends the sensitivity by searching for a given individual HPV sequence that enables detection down to 1 aM (individual molecules in the 5 microliter PCR volumes used in some embodiments). This increased sensitivity enables the detection of pathological HPV in the blood and serum, among other biological samples.

Moreover, the invention comprises systems, methods, and compositions to elaborate details of the type(s) of HPV associated with a given tumor and is sensitive, specific and quantitative, which cannot be done with certain currently used methods [1], which examine a combination of numerous probes and are not quantitative.

In some embodiments, without limitation, once the HPV type(s) is(are) determined in accordance with the invention, the invention also supports screening sensitively and specifically for the detection of that HPV at the single copy level in biological samples, including without limitation, in mammalian body fluids. Such a sensitive and specific screen at the single copy level has not been possible heretofore. It reveals a state of nature not previously established whereby presence of HPV in serum and/or blood is uniquely associated with dysplasia or cancer not seen in normal subjects. The lack of false positives as seen in reference [4] in such a screen makes it well-suited for determination of dysplasia or cancer.

In some preferred embodiments, without limitation, the invention comprises systems, methods, and compositions to determine the type and amount of pathogenic HPV that is present in a biological sample in a single test. In some embodiments, the invention comprises probes constructed using a mass spectroscopic assay system for one or more high or intermediate risk HPV types. Such high or intermediate risk HPV types may be selected according to identification using the Digene ThinPrep test [1], a current FDA-approved test for analysis of HPV in cervical scrapings. Some embodiments of the invention add to the 13 HPV types of the Digene test another 6 types of HPV that may be high risk to cause cervical and anal carcinogenesis [5, 6]. This determination can be carried out down to at least the 100 aM (ca. 300 molecule) level, an order of magnitude more sensitive than the current Digene method that requires several thousand HPV molecules to be positive [1]. Further, the present invention enables one to determine which type(s) of HPV are present in a tumor or dysplasia, or by extension, in materials derived directly from tumors (e.g., cervical ThinPreps). Finally, some embodiments of the invention comprise, without limitation, systems, methods, and compositions for quantitative analysis, in comparison to existing tests which are only qualitative. Coupling this quantitative determination with ascertainment of HPV type in accordance with the invention may have significant clinical utility [6], whereby clinical severity may be reflected by HPV copy number in different anatomic locations.

In accordance with some embodiments, without limitation, the presence of one or more types of pathogenic HPV in tumor or cellular extracts is detected by a sensitive and specific mass spectroscopic assay ([8-10]; FIG. 1). Generally the mass spectroscopic assay of the invention involves the amplification by PCR of a short nucleotide fragment found in HPV; digestion of primers and nucleotides; and extension of a "nested" mass spectroscopic assay primer with appropriate dideoxynucleotides. This results in the incorporation of a single dideoxynucleotide to the mass spectroscopic assay extension sequence only if the given HPV template is present from the first PCR reaction.

In accordance with some embodiments, the screen is set up in a manner where each sample is tested independently for one or more pathogenic HPV types, by way of one example only, 19 pathogenic HPV types, with distinguishable probe(s) that yields a characteristic signal if positive for a given type of HPV. It enables one to screen for a total of 19 HPV types, representing the core 13 types screened for originally (FIG. 1; HPV 16, 18, 31, 33, 35, 39, 45, 51, 52, 56, 58, 59 and 68 [1]), plus HPV types 23, 26, 53, 66, 73 and 82 that are potentially pathogenic [5].

Some embodiments also include a probe for a single copy fragment of total human genomic DNA (for example, and without limitation, a probe for a single copy fragment of an intron of the erbB-2 gene). In addition to highly sensitive screening at least down to the 100 attomolar (aM=$10^{-18}$ M) level, the present invention permits the determination of the type of HPV associated with a given tumor or dysplasia. Further, the determination of copy number of the HPV sequence is accomplished, which may also confer useful prognostic data [7].

In some embodiments, if this first screen described above is positive, the presence of HPV in body fluids is detected by an even more sensitive mass spectroscopic assay, using only the probe for the HPV type that was positive in the first screen. This is made possible by the use of the previous screen that details the type of HPV present in a given tumor or dysplasia. This technique affords the possibility of screening for recurrence of a tumor by testing blood and/or serum.

Sensitive detection of HPV in the serum and/or blood at the single copy level results in the unexpected and previously unappreciated results:

1. In accordance with the invention, cervical dysplasia can be detected by screening serum and/or blood. This has not been demonstrated before except by using a TaqMan-based technique which produces inaccuracy leading to a substantial fraction of normal cases yielding abnormal results [4]. In contrast, the present invention shows the unexpected and previously unappreciated result that a high fraction of cervical dysplasia cases is associated with HPV in serum and/or blood. By comparison, normal controls and successfully treated cervical dysplasia samples are free of this HPV in serum and blood. Before the present invention, the separate informativeness of serum and blood was not appreciated. This presumably arises from the distinct pathogenesis of these events; HPV in the serum arises from cellular lysis whereas HPV in the blood results either from either circulation of intact tumor cells or phagocytosis (with incomplete digestion) of tumor cells;

2. In accordance with the invention, it is shown unexpectedly that schistosomiasis-associated bladder cancer is uniformly associated with HPV. Previously, only one-half of these cancers were thought to result from HPV [11]. Extension to the more sensitive analysis of the invention at the single copy level also revealed that both serum (26/27 cases) and urine sediment (15/24) are useful for diagnosis. Blood HPV was not present even though serum HPV was positive in 26/27 cases;

3. Using the present invention, it is also shown that analysis of both blood and serum are useful for diagnosis and for monitoring the therapy of head/ neck cancers caused by HPV. Previously, although high levels of HPV often existed in tumors making this analysis feasible, the inability to detect lower levels made analysis of blood and serum impractical as most cases investigating serum were negative [3]. In contrast, detection in accordance with the present invention showed that a significant fraction of tumors were associated with HPV that could be detected in serum and/ or blood. This extended to a variety of pathogenic HPV types, evidence that this screen has clinical value as clinically insignificant HPV types do not interfere with the analysis; and 4. Using the invention, it was shown that all tested normal controls were negative, including all 40 normal urine sediments, all 27 normal serum samples, all 20 normal blood samples and all 9 placentae that were examined.

In some embodiments, without limitation, the invention comprises a two (2) stage screening method that is sensitive and specific enough to detect down to the single molecule level. The first stage involves screening the tumorous or dysplastic cells with a battery of all 19 pathogenic HPV types. Once the type of HPV is known, that type can be used to screen relevant body fluids with greater sensitivity than if all 19 sequences were to be used simultaneously. As a result, the screening of bodily fluids is of increased sensitivity and specificity to have improved clinical utility. In such a screen, serum and blood become informative independently, reflecting the different pathogenesis that yields HPV in these fluids. Presence of HPV in serum results from lysis of abnormal cells carrying HPV. Presence of HPV in blood results from presence of circulating tumor cells and/or phagocytosis of abnormal cells with detection of HPV sequences that are not fully digested. Thus, useful information results from the independent query of blood and serum. The invention comprises systems, methods, and compositions that extend to all body fluids (e.g., urine, cerebrospinal fluid, sweat, sputum, tears, etc.).

EXAMPLES

The following examples of some embodiments of the invention are provided without limiting the invention to only those embodiments described herein.

Figure 2:
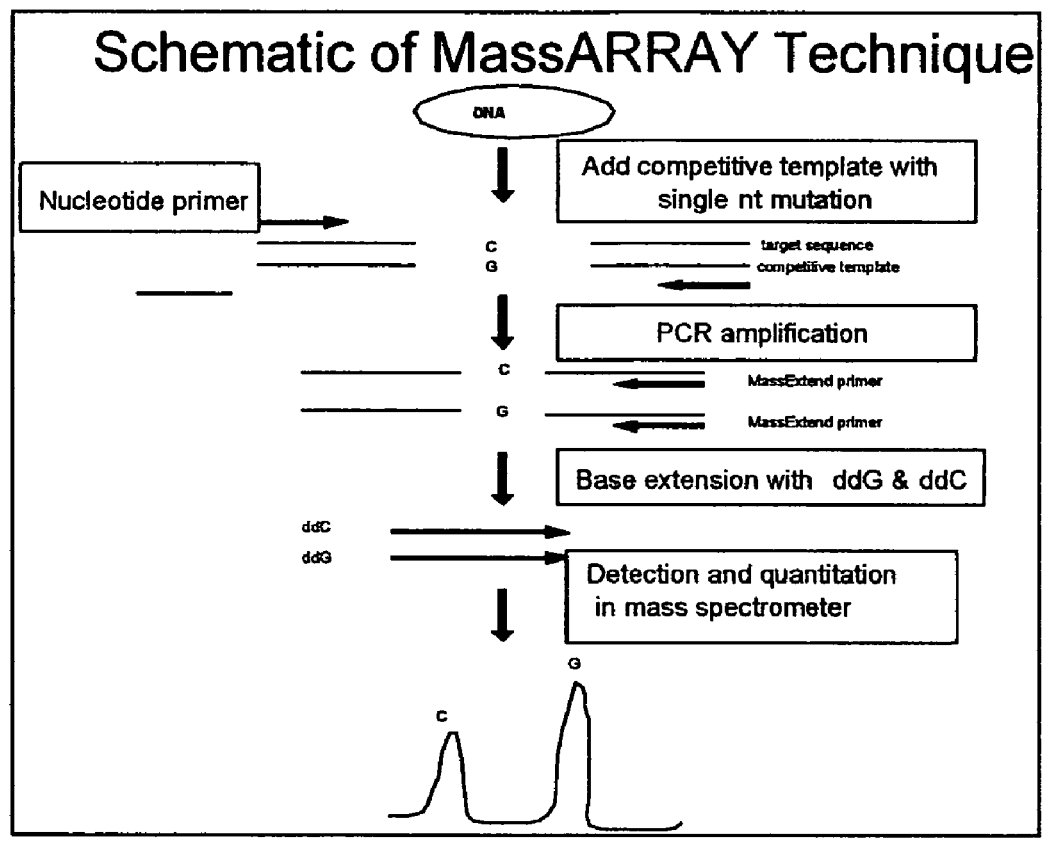
FIG. 2 is a generalized flow diagram of steps in accordance with some embodiments of the invention, without limitation.

In accordance with the some preferred embodiments, without limitation, the invention comprises the use of matrix-assisted laser desorption ionization—time of flight ("MALDI-TOF") mass spectrometry ("MS") for qualitative and quantitative gene expression analysis in combination with aspects of competitive PCR, primer extension reaction, and MALDI-TOF MS (see generally FIG. 2). A sample thought to contain HPV DNA isolated from a biological sample is spiked with a synthetic oligonucleotide ca. 100 nt long (the competitor) with a sequence identical to or substantially matching a portion of the DNA sequence of an HPV of interest except for one single base roughly in the middle of the sequence of interest. In some embodiments, the competitor is added in known concentration. The competitor and the DNA of interest are co-amplified by PCR in the presence of forward and reverse primers. Excess dNTPs and primers are removed by means known to those of ordinary skill after PCR, as one example only and without limitation, enzymatic digestion and appropriate washing. Then, a base extension reaction is carried out with an extension primer and a combination of different ddNTPs (as one example only, G and C). The extension primer hybridizes right next to the mutation site and at least one of two ddNTP bases is added differentially for the competitor and the DNA, yielding two oligonucleotide products with different molecular weights. In a typical molecular weight window of about 5,000 to about 8,500 Daltons (Da), the MALDI-TOF MS easily distinguishes two oligonucleotides if they differ by more than ca. 20 Da. In accordance with the invention, these differential extension products are identified qualitatively, and their concentrations can be quantified in relation to their ratio from the MALDI-TOF MS, as one example only, when the concentration of the added competitor sequence is known. In some embodiments, without limitation, desirable molecular weight spacing is further achieved by affixing, as desired, spacer molecules on the 5' end of the base extension primers, as described further herein.

Preparation and quantitation of DNA from samples. Tumor, serum, peripheral blood, and urine sediment samples were isolated at the time of tumor biopsy from individual persons with cancer. Serum and/or peripheral blood were isolated from normal controls not exposed to HPV, from individuals with schistosomiasis (with or without known bladder cancer), from individuals with schistosomiasis-associated bladder cancer after surgical removal of the tumor, from individuals with head/neck cancer, and from individuals with cervical or anal cancer or cervical dysplasia. Urine sediment was isolated from subjects with schistosomiasis-associated bladder cancer and from control subjects without bladder tumors. Urine sediment was the pellet isolated after centrifugation of urine for about 10 min at about 8,000 rpm in a Beckman J2-21M centrifuge. Placentas were obtained following normal births. Tissue, peripheral blood and urine sediment DNA were isolated using the ZR Genomic DNA I kit (Zymo Research Corp, Orange, Calif.). DNA was isolated from about 0.3-5 ml of serum using a ZR Serum DNA Isolation kit.

Cervical samples were collected in ThinPrep PreservCyt solution (Digene Corporation, Gaithersburg, Md.). Following reporting of patient results, specimens were unlinked to patient identifiers, and aliquots were prepared and tested by the mass spectroscopic PCR method. We isolated the DNA from about 5 ml of ThinPrep solution by rotating with about 10 μl of Zymo beads from the ZR Serum DNA Isolation kit. The beads were added to the sample and about 4 times the volume of Genomic Lysis Buffer (Zymo Research Corporation) was added. The mixture was tumbled overnight at about 4° C. DNA was prepared from the beads according to the manufacturer's directions. Final suspension was in a small volume (about 20 μl) of Elution Buffer. Samples were run for Digene HC2 and Roche analyses (including reverse line blotting) according to the manufacturers' instructions [1, 12]. Samples were then provided blindly for mass spectroscopic analysis in accordance with the invention.

To determine the amount of DNA in a given sample, we used TaqMan fluorescent QPCR [13] on the Bio-Rad iCycler for a unique intron in the erbB-2 gene. We used the primers 5'ACCTTCTCTTGACCTTTCAGAATATGT-3' (SEQ ID NO. 129) and 5'-AGAGAGTCTTGGCCCTTTCCA-3' (SEQ ID NO. 129), with the TaqMan probe 5'-AGAGGGCCCTCT-GCCTGCTGC-3' (SEQ ID NO. 130). We used the empirically derived value of $7.7 \times 10^3$ haploid genome equivalents/fluorescent unit of erbB-2 probe).

Construction of a degenerate TaqMan HPV DNA probe. A degenerate HPV DNA PCR probe was constructed in the L1 region of the virus [13]. The GP5+ and GP6+ primers were from de Roda Husman et al. [15]. The MY18 and MY1019 primers were from Nelson et al. [16]. To construct a degenerate TaqMan [13] set, we combined the sequences to yield a TaqMan set with the 2 outside primers (based on GP5+ and GP6+) and a probe (based on MY18 and MY1019). Melting temperatures ($T_m$) were derived using the oligo calculator of Qiagen (http://www.operon.com/oligos/toolkit.php?).

Primer 1 (GP5+ analogue): The GP5+ analogue was constructed by combining an equal amount of each of the 4 primers listed below:

GCACAGGGACATAATAAT (SEQ ID NO. 131)   $T_m$ = 53.8° C.

GCACAGGGTCATAATAAT (SEQ ID NO. 132)   $T_m$ = 53.8° C.

GCCCAGGGACATAAT (SEQ ID NO. 133) $T_m$ = 53.8° C.

GCCCAGGGTCATAAT (SEQ ID NO. 134) $T_m$ = 53.8° C.

Primer 2 (GP6+ analogue): GMTATGATTTACAGTU-ATTTTTC (SEQ ID NO. 135) $T_m$=53.1° C.

Probe: The MY1019 final probe was constructed by mixing an equal volume of MY1019 analogue 1 and MY1019 analogue 2. The final probe was constructed from an equal amount of the MY18 analogue and the MY1019 final analogue.

MY18 analogue: CTGTTGTTGATACTACACGCAGTAC (SEQ ID NO. 136) $T_m$=62.8° C.

MY1019 final analogue was constructed from a 1/1 mixture of:

MY1019 analogue 1: GTGGTAGATACCACACGCAGTA (SEQ ID NO. 137) $T_m$=.63.4° C.

MY1019 analogue 2: GTGGTAGATACCACTCGCAGTA (SEQ ID NO. 138) $T_m$=.63.4° C.

The primers and probes were synthesized at our request by Biosearch. The probe was labeled with the fluor 6-FAM at the 5'-end and Black Hole Quencher 1 at the 3'-end. We tested the degenerate primer-probe collection on plasmids carrying either HPV-16 or HPV-18 sequences (American Type Culture Collection), respectively. Using the degenerate probe, we obtained equivalent amplification with either plasmid.

PCR amplification of degenerate TaqMan probe. Since all normal sera contain small amounts of normal genomic DNA [16], we verified that serum DNA was prepared from all samples with a TaqMan erbB-2 genomic DNA probe [13]. In a similar manner, we confirmed that DNA was isolated from all other samples used. Following denaturation at about 95° C. for about 5 min, a two step program of denaturation at about 95° C. for about 15 sec and annealing at about 60° C. for about 30 sec was employed to amplify erbB-2 for 40 cycles. Following denaturation at about 95° C. for about 5 min, the conditions we used for QPCR amplification for HPV DNA on a Perkin-Elmer model 7700 after optimization were a two step program of about 52° C. for about 60 sec (for annealing and extension), and denaturation at about 95° C. for abort 15 sec for 40 cycles. We also performed this for about 55 cycles for a number of samples to match the 55 cycles used in the last amplification step of the mass spectroscopic-PCR method. The lower than normal annealing and extension temperature of about 52° C. reflected our use of a degenerate probe. For the TaqMan reaction with the degenerate HPV DNA probe, each value was repeated in quadruplicate. Samples were analyzed by the TaqMan method [13] on a Perkin Elmer model 7700 machine. DNA sequencing was done by the University of Michigan Core sequencing facility.

Application of HC2 method. The HC2 reaction includes RNA probes complementary to the DNA of each of 13 high-risk types of HPV. Hybridization between HPV DNA and any of the complementary RNA probes is detected using capture antibodies which target RNA:DNA hybrids [1]. Specimens with relative light unit (RLU) cutoff ratios $\geq$10 on initial testing were considered positive. Specimens with RLU cutoff ratios <about 0.8 were considered negative. Specimens with RLU cutoff ratios from about 0.8-9.99 were tested again. If the repeat RLU cutoff ratio was $\geq$1, the sample was considered to be positive. Ambiguous specimens that did not repeat as positive were not included in this study. The samples were split into 2 groups (HC2 (+) and HC2 (−); anonymized and excess ThinPrep material was studied by the MassARRAY technique.

Alternative analyses of HPV type. As indicated, we derived the HPV type of selected samples by the Roche method of reverse line blot analysis [12]. Alternatively, we used degenerate primers in the L1 region of HPV to detect the most abundant HPV sequence that could be amplified by these degenerate primers [15, 17]. This worked for all of the 13 pathogenic types of HPV except HPV52 (where in our test the divergence between HPV52 and the degenerate primers was too great to allow primer binding).

Measurement of human genomic DNA. To determine the amount of DNA in a given sample, we used TaqMan fluorescent QPCR [12] on the Bio-Rad iCycler for a unique intron in the erbB-2 gene. The primers were 5'-ACCTTCTCTTGAC-CTTTCAGMTATGT-3' (SEQ ID NO. 139) and 5'-AGAGAGTCTTGGCCCTTTCCA-3' (SEQ ID NO. 140), and the TaqMan probe was 5'-AGAGGGCCCTCTGCCT-GCTGC-3' (SEQ ID NO. 141). We derived a value of $7.7 \times 10^3$ haploid genome equivalents/ fluorescent unit of erbB-2 probe. We have also incorporated a probe for this intron into a mixture of 22 probes that are analyzed by the mass spectrometer (Table 1) and no longer require separate analysis on the iCycler.

Quantitative mass spectroscopic method of analyzing PCR. In accordance with some embodiments, without limitation, the invention comprises a multi-step process of real-time competitive PCR (rcPCR), primer extension and MALDI-TOF MS separation of products on a matrix-loaded silicon chip array to detect as few as several initial molecules [8]. A competitive nucleotide template (as one example only, ca. 100 nt) is synthesized to match an HPV target sequence for PCR except for a single base mutation in the competitor, which is introduced during the synthesis. The single base change can then be discriminated from the HPV target allele using a primer extension reaction with product resolution by mass (in Daltons) on the MALDI-TOF MS as is done analogously for SNP genotyping [10]. Preferably, but not exclusively, the competitive template is added to the PCR reaction at known quantities and can therefore be titrated to create a standard curve for the determination of target DNA quantities. When the peak areas of the target allele and competitive template allele are equal, the concentrations of the two molecules are at about a 1:1 ratio, representing the amount of target DNA in the reaction. The mass spectroscopic analysis is very specific as, in this exemplary embodiment, a given primer extension product was discerned down to a resolution of ca. 20 daltons. Any contaminant products would therefore have to be this specific size to create a false-positive signal. The presence of the internal standard (competitive template) also serves to confirm that the enzymes required for PCR were working and that the sample was purified free of inhibitors of PCR.

Determination of HPV type and amount with real-time competitive PCR and mass spectroscopic analysis of DNA. In accordance with some embodiments, without limitation, a 13-plex HPV assay was designed by first deriving PCR and extension primer sequences with Primer3 software (http://frodo.wi.mit.edu/cgi-bin/primer3/primer3 www.cgi) from the E6 region of the various HPV strains. These sequences were then used to define input sequence boundaries for use with MassARRAY assay designer software v3.0. (Sequenom, Inc., San Diego, Calif.) [8]. In this manner, we were able to distinguish each of the 13 discrete types of high-risk HPV (FIG. 1) [1]. Forward and reverse primer, extension primer, and competitor sequences are disclosed in Table 2. Some embodiments also comprise a more intensive screen using different software we elaborated that is customized for this purpose. Using this software, we constructed a probe comprised of 22 sequence types that includes the original 13 types of HPV, 6 additional types of HPV, a genomic DNA single copy probe to allow quantitation of the amount of human DNA in a given aliquot, and probes for *Neisseria gonorrhoea* and *Chlamydia trachomatis* (see e.g. Tables 1A-1C). The temperature for the first PCR reaction is about 60° C. and the temperature for the second primer extension reaction is about 58° C.

Conditions for multiplexed rcPCR mass spectroscopic analysis of PCR have been described previously [18, 19]. Reactions were initiated by creating a 96 well master plate from which a 384 well reaction plate was established using a MultiMek robot. There were 4 wells at 0 aM (attomolar = $10^{-18}$ M) of a given competitor and 4 wells at 1 aM of a given competitor for each HPV strain. Reactions that were positive for a given HPV sequence were then quantified for each of the positive HPV(s). We quantified the reaction using 10 aM, 100 aM and 1 fM (femtomolar=$10^{-15}$ M) of competitor. If a reaction was still too positive to be titered, the specimen was diluted 1/100 and re-titered.

Because MassARRAY is not a homogeneous assay, attention should be paid to setting up the reaction. We used two robots (before and after the initial PCR) to set up reactions and minimize contamination. The routine control in every plate showing that normal samples were negative confirmed that these techniques to prevent contamination were effective. All values reported herein represent the analysis of at least 8 independent data points.

Control samples. We examined a series of controls for tissue, serum, peripheral blood and urine sediment. The tissue controls were DNA samples from normal placentas. The serum and peripheral blood controls were DNA samples we isolated from sera and peripheral blood of anonymous subjects not known to be exposed to HPV. The urine sediment controls were DNA samples from normal volunteers. In all the cases reported herein, reaction with an erbB-2 control probe by TaqMan was positive, confirming that DNA of QPCR quality was present. The control samples were usually negative for the degenerate HPV DNA probe in all 4 wells and rarely were positive in 1/4 wells. Thus, we conservatively only took samples that reacted in ≧3/4 wells to be positive.

Using the definition above on samples analyzed on the Perkin-Elmer model 7700, the degenerate HPV DNA probe reacted with 0/40 normal urine sediments, 0/27 normal serum samples, 0/20 normal peripheral blood samples and 0/9 placentas (control for normal tissue samples). Further, an even more sensitive analysis with the mass spectroscopic-PCR system also showed that no HPV DNA was present in any of these normal samples.

Using the highly conserved reverse primer (GP6+ analogue) as the initiating primer for DNA sequencing, we were then able to determine the HPV DNA type by dideoxy sequencing. We observed the following:

The degenerate probe was appropriately negative in all control tissues; and

We saw evidence of HPV DNA in schistosomiasis-associated bladder cancers (Table 3), head/ neck cancers (Table 4), and cervical cancers (Table 5). This is in agreement with a large body of literature that suggests such involvement.

By way of additional examples only, without limiting the possible embodiments of the invention, in a first stage, tumors or cervical ThinPreps were screened for one of the 13 pathogenic types [1], using the mass spectroscopic assay of the invention to identify separately any of the 13 different types of pathogenic HPV in a single reaction. Sequences from the E6 region of HPV that must be present for HPV to transform a cell were derived. The E6 protein of oncogenic HPV strains interacts with the p53 protein and promotes its degradation via a ubiquitin-dependent pathway [20]. Sequences were derived from the E6 region of each of the 13 types of HPV that are pathogenic for human cancer (http://hpv-web.lanl.gov/) and are known according to at least one existing method, the Digene screen [1; Table 2].

In some embodiments, without limitation, sequences are adjusted to obtain good molecular weight spacing without undue variation of primer size that could alter optimal temperatures for PCR. We used this methodology for our more advanced screen with 22 probes as detailed in Tables 1A-1C. In some embodiments, there is use of no more than 15 contiguous bases, with substitution of the "wild card" base deoxyinosine for deoxyguanosine, deoxyadenine, or deoxythymidine. This concept is derived in relation to the size of the human genome, so that the number of permutations afforded by 16 or more bases (ca. $4^{16}$) is larger than the human genome size. Using such embodiments, we found that the substitution of an internal deoxyinosine had no effect on PCR conditions or performance of the PCR assay. The primers we used for the 22 target sequences are listed in Table 1. Thus, in these embodiments, we did not use a stretch of sequence >15 nucleotides, which otherwise has been related to given sequence in the human genome (a sequence must be this long to be represented uniquely in the human genome). Thus, in some embodiments, contiguous sequences used are too small to be represented uniquely in the human genome.

Moreover, in some embodiments, without limitation, desirable molecular weight spacing was also achieved by affixing, as desired, spacer molecules on the 5' end of MassEXTEND primers (e.g., Tables 1B and 1D), the internal primers used for the mass spectroscopic assay approach utilized [8]. Suitable spacer molecules include, without limitation, phosphorylation, C3 spacers, D spacers, amino modifiers C12, spacers 18, and amino modifiers C6 available from Integrated DNA Technologies (Coralville, Iowa). This achieves the desirable spacing of our primer sequences without making major changes in primer length that would affect PCR condition, thus maintaining optimal PCR conditions for all primer sets at uniform conditions to optimize PCR. Taken together, the approaches of using deoxyinosine and modifiers yield a set of primers adapted for this approach, as used in some embodiments.

In some embodiments, the sequences were chosen so there was no molecular weight overlap <ca. 20 nt between the sequences corresponding to the unextended primer, the wild type gene, and the internal competitor for each of the 19 different types of HPV. We also added probes for *Chlamydia trachomatis* and *Neisseria gonorrhoea*, so that in the end this technique may detect and quantitate 19 types of HPV, a standard to read out how much genomic DNA is being analyzed, and a determinant for infection by *Chlamydia* or *gonorrhea*. In all, such a system will discriminate each of the 3×22=66 different peaks (the peaks distinguished by mass spectrometry were unextended primer; unextended primer+ wild type gene sequence (unextended primer plus either a C or G, depending on the next nucleotide of the gene); and unextended primer+internal competitor sequence (unextended primer plus either a G or C, depending on the next nucleotide of the competitor). These distinctions were based on the ability of the mass spectrometry-based method to distinguish a separation of ca. 20 daltons between 2 molecular weights.

FIG. 1 depicts the profile results of a mass spectroscopic assay screen in accordance with the invention for the 13 pathogenic types of HPV that are screened for in the Digene test [1] (HPV 16, HPV 18, HPV 31, HPV 33, HPV 35, HPV 39, HPV 45, HPV 51, HPV 52, HPV 56, HPV 58, HPV 59, HPV 68). The 13 different peaks corresponding to the molecular weights of the MassEXTEND primer [16] for each of the 13 distinct high-risk HPV types (HPV 16, 18, 31, 33, 35, 39, 45, 51, 52, 56, 58, 59 and 68 [3]) are shown. The lines without peaks denote where the MassEXTEND competitors and gene products would map (representing a potential total of 3×13=39 non-overlapping peaks; for simplicity, only the 13 unextended peaks are shown).

FIG. 1 illustrates the invention's ability to detect and distinguish a variety of HPV DNA sequences. In some embodiments, we used an appropriate set of outside primers and an appropriate unextended primer MassExtend sequence (ca. 20 nt) for each ca. 100 nt HPV E6 sequence, for the genomic DNA standard, for *Chlamydia trachomatis*, and for *Neisseria gonorrhoea*. An oligonucleotide corresponding to each of the ca. 100 nt sequences was synthesized, with one base changed (a C for a G, or a G for a C). The synthesis was done, for example, using a commercially available oligonucleotide synthesizer (e.g., service afforded by Integrated DNA Technologies (IDT)). Ca. 100 nt long oligonucleotides were synthesized using sequences corresponding to the internal competitor sequence for each of the 19 different types of HPV, the genomic DNA standard, *Chlamydia trachomatis*, and *Neisseria gonorrhoea*. For each of the 22 sequences, ca. 20 nt primers (to which tags were added to eliminate interference with the mass spectroscopic profile shown in FIG. 1) were synthesized corresponding to the right and left ends of these ca. 100 nt long oligonucleotides. Finally, a mass spectroscopic assay extension primer was synthesized, comprising a sequence directly abutting a C or G (in which case the internal competitor resulted in the incorporation of a G or C, respectively. that it was possible to distinguish the wild type gene sequence from the internal competitor sequence) using this one nucleotide difference.

In some embodiments, the primer sequences are identical for the wild type gene sequence and internal competitor. The only difference between the wild type gene sequence and internal competitor is the one nucleotide adjacent to the unextended primer sequence. Given this identity of sequence, both the wild type gene sequence and the internal competitor amplify with the same efficiency. As a result, amplification of a known amount of the internal competitor can be used in the invention to quantitate the amount of the wild type gene sequence that is amplified.

In some embodiments, without limitation, the unextended primers, unextended primers+guanosine and the unextended primers+cytosine (3×22 primers=66 total primers) should all fit in a molecular weight space between about 5000 and about 8500 daltons, and be separated by a minimum distance of ca. 20 daltons. At the same time, the length of the primers are constrained by the requirement that they bind and function as templates within a small temperature range so that they will all yield amplification at the same temperature. To accomplish these goals, we developed the novel strategy of affixing various inert spacer molecules to the 5' end of the unextended primer.

For some embodiments, without limitation, the amplification primers used for the first PCR amplification are given in Table 1A. The primers used for PCR-mediated extension are given in Table 1B. The sequences of the competitors are given in Table 1C. The spacers we used are detailed in Table 1D. Primer sequences are given for HPV types 16,18, 23, 26, 31, 33, 35, 39, 45, 51, 52, 53, 56, 58, 59, 66, 68, 73 and 82. We also include a measure of total genomic DNA input using an intron of the gene erbB-2, and probes for 2 infections of gynecological import (*Chlamydia trachomatis* and *Neisseria gonorrhoeae*). The primer sequences have been tested and found to be operational. As a result, the invention comprises screening simultaneously for 19 types of HPV, a measure of total genomic DNA and tests for infection by *Chlamydia trachomatis* and *Neisseria gonorrhoeae*.

The methodology of this embodiment may be used seamlessly with other aspects of the invention described herein to determine the type and amount of HPV present in serum and/or blood, including but not limited to, due to tumorigenesis. Since the technique of screening serum and/or blood is maximally sensitive when screening the HPV probe of choice, the screen of tumor and/or ThinPreps may be used to determine whether HPV is present, and if so, which type of HPV. That type of HPV is then used to screen blood and/or serum with maximum efficiency; if several types of HPV are present, each type can be screened for individually. The success of this embodiment of the invention utilizes the presence of HPV in tumor or ThinPreps at concentrations higher than in serum and/or blood. Once the type of HPV is determined, the serum and/or blood can then be screened with maximal sensitivity for the HPV type found in the tumor.

As discussed above, the Digene test does not reveal which HPV type is found in the cervix ThinPrep. This becomes important as the invention as applied to serum and/or blood in some embodiments is most sensitive when only a known single pathogenic HPV type is screened for rather than a general screen for all 13 pathogenic types of HPV. Given that there is often so little HPV DNA present in serum and blood of cancer and dysplasia cases, the user may prefer to do this screen with only one HPV probe at a time to increase sensitivity, even with the sensitive mass spectroscopic assay analysis of the invention [3].

Without limitation, some preferred embodiments of the invention address shortcomings of the Digene reaction by:

1. Comprising an application of the multiple capabilities of the mass spectroscopic assay screen;

2. Accurate diagnosis without cross-reaction from related HPV sequences occurs because the molecular weight of each HPV type-specific reaction product is accurate to ±ca. 20 daltons, so it is specific for the sequence of a given HPV type. In fact, the mass spectroscopic assay test of the invention distinguishes each of the 13 pathogenic types of HPV detectable by the Digene screen without cross-reaction with other HPV viruses (FIG. 1);

3. The mass spectroscopic assay of the invention is positive down to the level of individual molecules (at which level one may see expected Poissonian variation); and 4. The mass spectroscopic assay reaction of the invention distinguishes which HPV type is present in the cervix ThinPrep. Since the technique of screening serum and/or blood is maximally sensitive when screening the HPV probe of choice, the screen of tumor and/or ThinPreps is used to determine whether HPV is present, and if so, which type of HPV. That specific type of HPV is then used to screen blood and/or serum with maximum efficiency. The success of this screen utilizes the presence of HPV in ThinPreps of cervix scrapings or in tumors at concentrations higher than in serum and/or blood. Once the type of HPV is determined in the ThinPrep or tumor, the serum and/or blood can then be screened with maximal sensitivity for the HPV type found in the tumor.

In some preferred embodiments, without limitation, in a second stage (Stage 2) of the invention, once an HPV type is identified, body fluids (such as serum and blood) or recurrent tumor or repeat ThinPreps are screened with the indicated HPV type determined in Stage 1. These studies may be performed longitudinally to determine whether the type and persistence of HPV has prognostic uses, as one example only and without limitation, to determine whether residual tumor is present in an individual previously treated for the disorder. Without the invention, such investigations were not possible because the analyses of HPV in serum and/or blood were not sufficiently sensitive or specific [3] even when the analyses were performed with TaqMan technology. In contrast, our current studies using the invention demonstrate the feasibility of both serum and blood studies with the sensitive and specific Mass spectroscopic assay technique of the invention.

As another example, without limitation, in some embodiments comprising the mass spectroscopic assay system, HPV 16 DNA was detected in all 24 schistosomiasis-associated bladder tumors from which DNA was prepared DNA (right side of Table 3). In all but one of these samples, the matching sera were also positive. In an additional 3 cases for which tumor DNA was not available, the sera were positive for HPV 16 DNA. HPV 16 DNA was detected in urine sediment from most, but not all, of the schistosomiasis-associated bladder cancer cases. These data implicate HPV 16 infection in schistosomiasis-associated bladder cancers. By comparison, real-time TaqMan QPCR was not as sensitive (left side of Table 3) as mass spectroscopic assay analysis of some embodiments (right side of Table 3). Blood (buffy coat) from these cases was uniformly negative by both real-time QPCR and mass spectroscopic assay (data not shown). Abnormal readings documenting the presence of HPV DNA are bolded. Attomolar (aM)=$10^{-18}$ M; femtomolar (fM)=$10^{-15}$ M; with the 5 µl volumes we used for PCR, 1 aM corresponds to ca. 3 molecules.

Comparison of mass spectroscopic assay results of the invention (right side of Table 3) with older in situ hybridization data [10] and TaqMan data for a standard 40 cycles (left side of Table 3) shows that the invention is more sensitive than either in situ hybridization or TaqMan QPCR. The lack of reproducibility of the data on the left side of Table 3 (data not shown) indicates that the TaqMan technique is operating at the limits of its sensitivity and is not accurate. Further, the TaqMan technique does not distinguish quantitatively between tumors, serum, and urine sediment. TaqMan RT-QPCR for 55 cycles was also attempted in order to mirror the mass spectroscopic assay method of some embodiments. No improvement between signal and noise was observed, underscoring the limitations of the TaqMan technique. In contrast, the values on the right side of Table 3 that are derived from the invention are consistent with the expected finding that tumors are more positive than serum and/or urine sediment.

In this example, both specificity and sensitivity were maintained in a mass spectroscopic assay embodiment of the invention. Using the invention, HPV 16 DNA was detected in all schistosomiasis-associated bladder tumors examined (24/24), in nearly all (26/27) sera from these cases and in a majority (15/24) of urine sediments from these cases. Blood from these cases did not contain detectable HPV DNA (data not shown).

In related examples, it was shown that the presence of HPV DNA is not simply due to schistosomiasis. 10 cases were examined where schistosomiasis existed and there was some question of bladder cancer that could not be proven clinically. In 8 of the cases, there was no HPV 16 or HPV 18 DNA found in the serum; in 2 of the cases, HPV 16 DNA was found. This demonstrates that HPV DNA is not associated with schistosomiasis per se, but rather with tumor development in schistosomiasis cases with bladder cancer. It also illustrates the use of the invention to aid diagnosis in equivocal cases where the clinical data is suggestive but not conclusive.

It was also shown that serum HPV 16 DNA disappears rapidly after tumor removal. The sera of 7 subjects with schistosomiasis were examined within 2 weeks after surgical removal of a cancerous bladder. In all 7 cases, there was no HPV 16 DNA detected in serum. While sera prior to surgery were not available, the uniform positive nature of the tumors for HPV 16 (Table 3) indicates that HPV was likely present and then eradicated by surgery.

Whether HPV DNA was present in matched tumor, blood and serum samples obtained at the time of diagnosis of head/neck cancer was also investigated. For each sample, the site of the primary tumor is given. Analysis with TaqMan fluorescent QPCR was also attempted but did not detect HPV DNA in blood and serum, in agreement with the finding by others that the TaqMan technique is not sufficiently sensitive to be clinically useful [3, 21]. In contrast, mass spectroscopic assay analysis in accordance with the invention yielded the data summarized in Table 4. Readings documenting the presence of HPV 16 DNA are bolded.

Tumor, serum and blood were isolated from cases of head/neck cancers (not all sample types were available for all subjects; the lack of a sample is denoted by a blank space). Mass spectroscopic assay determination of HPV 16 DNA was done on these tumor, blood and serum samples; none of these samples were positive with the HPV 18 DNA probe, although another head/ neck tumor sample on which we did DNA sequencing was positive for HPV 18 DNA. Abnormal readings documenting the presence of HPV DNA are bolded. Attomolar (aM)=$10^{-18}$ M; femtomolar (fM)=$10^{-15}$ M.

There was a strong bias for tumors in the anterior parts of the head/neck tract (e.g., tongue, tonsil) to be positive for HPV and for tumors in the posterior parts (e.g., larynx, supraglottic region) to be negative. This is consistent with previous reports [22-29]. We saw only 3 oral tumors (out of 16) that were negative for HPV 16 DNA and HPV 18 DNA (the negative oral tumors could still be positive for other types of HPV). We saw only 1 tumor out of 10 (the hypopharyngeal tumor) that was posterior to the oral cavity and was positive for HPV 16. From the 9 samples where tumor was positive and both blood and serum could be analyzed, there were cases where the tumor was positive for HPV DNA in which HPV DNA was discerned in the serum only, blood only or in both the serum and blood.

Cervical cancer is almost uniformly associated with HPV [16, 22]. Using a mass spectroscopic assay in accordance with the invention for the 13 high risk human papillomavirus (HPV) sequences in cervical tumors and dysplasias, we saw that:

1. Virtually all tumors had evidence of one of the 13 pathogenic types of HPV with the amount of pathogenic HPV type decreasing continuously to zero. Non-pathogenic HPV was seen in dysplasias but essentially absent tumors, supporting the concept that a restricted group of HPV types is responsible for cervical carcinogenesis. The unique ability of the mass spectroscopic assay to detect down to the level of few viruses enabled us to detect pathological HPV types even at miniscule levels not feasible by other methods;

2. In cervical tumors, the HPV titers were routinely less than 1 HPV molecule/haploid tumor genome, several orders of magnitude lower than in the highest values seen in dysplasias. This is consistent with a 'hit and run' model whereby HPV infection is necessary for growth of dysplasias, but not sufficient for oncogenesis;

3. Virtually all pathologically abnormal (CIN 1 or 2) cervical dysplasias exhibited one of the 13 types of pathogenic HPV. We often saw multiple types of pathogenic HPV at differing titers. These multiple infections with pathogenic HPV were more common in the pathologically abnormal dysplasias than tumors (72% vs. 17%). In addition, using other methodologies, we often detected other HPV types present at higher titers in dysplasias. However, we did not detect these types in tumors, demonstrating that tumorigenesis results from a restricted set of HPV types that are covered by our mass spectroscopic assay; and 4. The detection of other HPV types by the currently clinically used Digene HC2 method is responsible for the false positives resulting from this test. The mass spectroscopic assay mitigates this problem.

Current methods to detect cervical disease rely on two major technologies: 1. detection of cytological anomalies of exfoliated cervical cells, the 'Pap' smear developed by Dr. G. N. Papanicolaou [30]; and 2. detection of HPV infection [1]. The major drawbacks of cytology are the problematic inter-observer reliability, limited sensitivity ($\leq 85\%$) and reliance on highly-trained individuals to perform tests [30, 31]. Indeed, it is only by repetitive screening that the sensitivity of Pap smears is considered adequate for clinical purposes. Consequently, the loss of individuals to regular follow-up and the inability of even repeated uses of the cytological Pap test to detect all individuals with cervical abnormalities both contribute to the cervical cancer incidence in screened populations.

An alternative to cytologic methods is to accomplish direct detection of HPV, a necessary cause of virtually all cervical carcinomas [1, 5, 32]. HPV is currently detected by either the FDA-approved HC2 test™ (Digene Corporation, Gaithersburg, Md.) [1], that uses a cocktail of type-specific hybridization probes to detect 13 types of high-risk HPV associated with cervical malignancies PCR using degenerate oligonucleotides [15, 33, 34] or a suite of diagnostic tests by Roche [35] that detects and then types the form of HPV that is present [1]. The major drawbacks to these methods are limited sensitivity, specificity and quantitative abilities. Sensitivity is limited as ca. $10^2$ -$10^3$ molecules are required to be detected by these tests [1, 13]. Specificity is limited due to cross reaction of HC2 with non-high-risk strains of HPV. ca. 10% of the time due to cross reaction with non-high-risk strains of HPV [2] [2, 36]. In addition, the HC2 test does not allow permit facile for accurate quantitation. Quantitative differentiation by HC2 is limited as normalization to the total cellular content is rarely done, the variability of the test is limited and it is not possible to quantitate which type(s) of HPV are responsible for the an observed signal when multiple HPV sequences are present. Using the Roche suite of techniques to deal with these limitations requires multiple types of testing that make the examination more difficult to accomplish. Because of these difficulties, quantitation is intricate and rarely performed.

In contrast, we disclose an invention comprising a mass spectroscopic assay-based approach to monitor cervical dysplasia, whereby type-specific discrimination and quantitation of cervical HPV can ultimately be coupled to blood and serum testing. In some of our work, we used the same 13 HPV types as detected in the FDA-approved HC2 method for high-risk strains (HPV 16, 18, 31, 33, 35, 39, 45, 51, 52, 56, 58, 59 and 68) [1]. The primer sequences and molecular weights, and the competitor sequences, are given in Table 2.

Figure 3A:
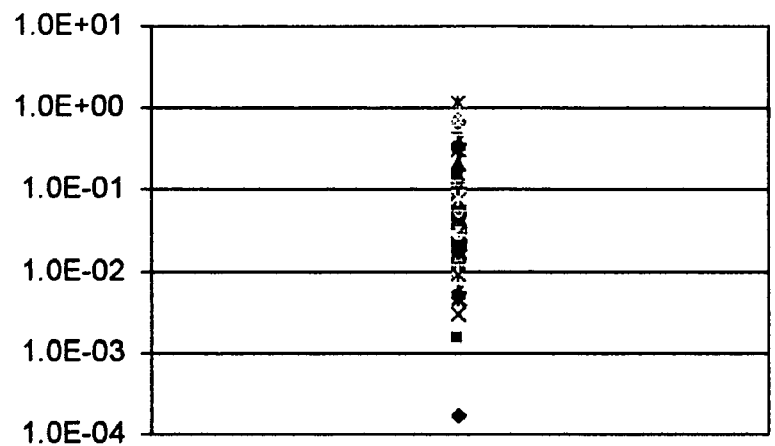
Figure 3B:
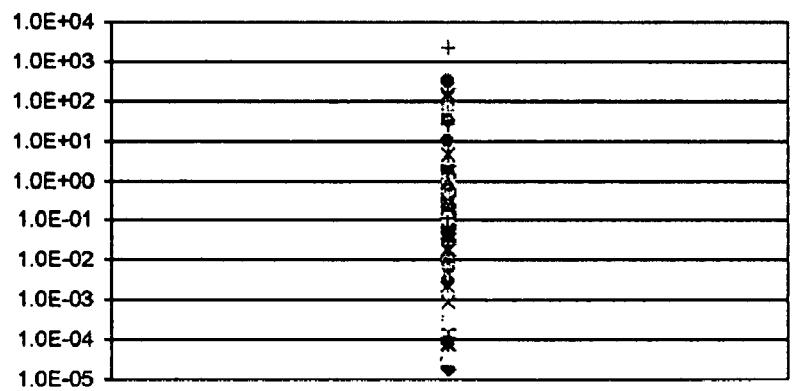
Figure 3C:
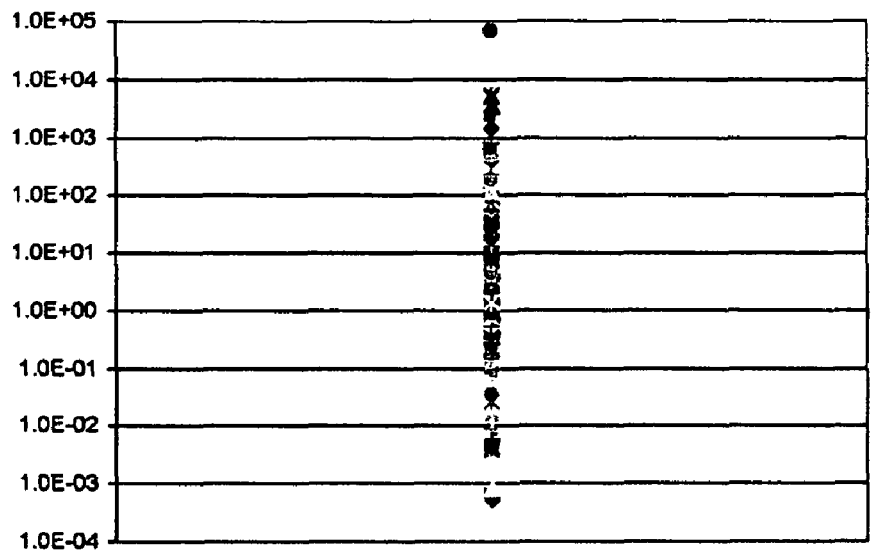
Figure 3D:
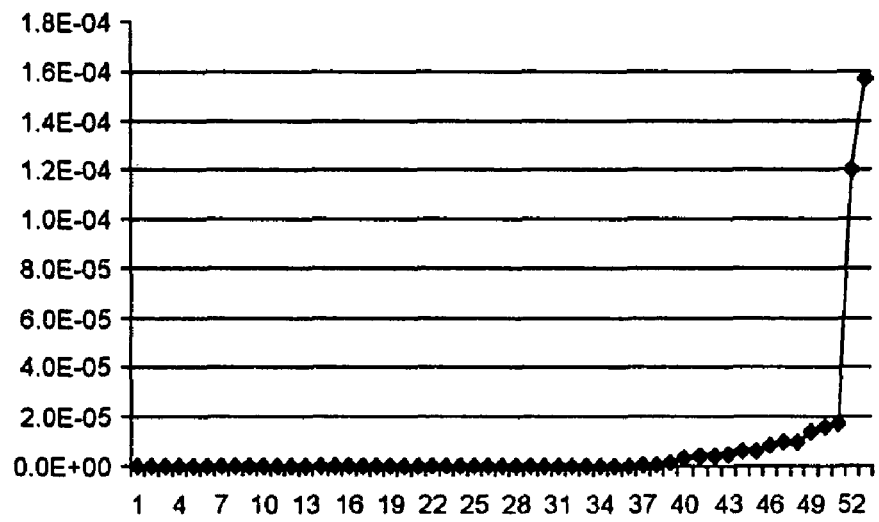

Using the mass spectroscopic assay of some embodiments, we saw an appropriate complete absence of HPV in 35 blood control samples when investigated with probes for thirteen (13) HPV types (data not shown). This demonstrates that this highly sensitive technique does not generate a background of false positives. Several points will emerge from our data: First, we observed samples with each of the pathogenic 13 HPV types uniquely, so that there is not cross reaction between HPV types in the mass spectroscopic assay. Supporting this point, there was no consistent HPV type found with another HPV type when multiple types were present. Second, the mass spectroscopic assay attains sensitivity at the level of individual molecules as confirmed by Poissonian variation observed at these lowest levels. Third, multiple HPV infection with these 13 types is more common in dysplasias with CIN I/II (72%=70/97) than in HC2 positive lesions (32%=36/113) than in tumors (17%=13/78). Fourth, the viral titers per cell are higher in dysplasias than in tumors (the values for tumors uniformly indicate <1 copy of HPV per haploid genome equivalent (FIG. 3A) whereas the values range through about $10^3$ copies of HPV per haploid genome equivalent in Pap positive dysplasias (FIG. 3B) and $10^4$ copies of HPV per haploid genome equivalent in HC2 positive dysplasias (FIG. 3C)). Thus, the median values of the most abundant HPV sequence for a sample were about $8.4 \times 100$ for the HC2-positive samples, about $3.0 \times 10^{-1}$ for the CIN I/II samples, and about $2.9 \times 10^{-2}$ for the tumors. Thus, the median HPV titers are one to two orders of magnitude lower in tumors than dysplasias. By comparison, most samples from women with normal Pap smears did not have HPV or only had low titers of HPV (FIG. 3D). Fourth, one of the 13 pathogenic HPV types was present in virtually all cervical tumors (81/82; Table 5). In all cases, the amounts of pathogenic HPV varied continuously down to zero copies/ haploid genome.

This included the tumor samples for which only the mass spectroscopic assay was sufficiently sensitive to detect the HPV types at the lowest titers. We detected very low amounts (down to about 1 aM=individual molecules) of HPV by mass spectroscopic assay which was not possible with other less sensitive techniques. The finding that virtually all tumors carried one of the 13 pathogenic types of HPV was confirmed by DNA sequencing primed with a degenerate primer as described in Materials and methods (Table 5). Except for failures of DNA sequencing due to an insufficient number of molecules available for DNA sequencing, we routinely confirmed the mass spectroscopic assay results that the associated HPV types were one of the 13 high risk HPV types.

There was excellent concordance between the HPV types detected by the mass spectroscopic assay and the types detected by degenerate DNA sequencing. There were a few disagreements that can be expected since the 2 techniques have different targets and thus diverge. In a case with a mass spectroscopic assay result of only about 2 aM for HPV 31, the DNA sequencing detected HPV 73, a type not seen in the 13 pathogenic types of HPV (but which is in our newer screen for 19 HPV types). Thus, this tumor had both HPV types, with the pathogenic HPV 31 below the detection ability of DNA sequencing. There were 3 other cases of discordance between the mass spectroscopic assay and DNA sequencing results, but in each case only HPV types belonging to the group of 13 pathogenic types was identified by DNA sequencing.

Mass spectroscopic assay, reverse line blotting and degenerate DNA sequencing on pathological cervical dysplasias. We compared the results of mass spectroscopic assay with reverse line blotting [12] for pathologically abnormal samples determined to have dysplasia staged at cervical intraepithelial neoplasia CIN I or CIN II. For 49 samples, when the mass spectroscopic assay technique demonstrated the presence of one of the 13 pathogenic HPV types at a concentration of at least about 40 aM, there was complete agreement between mass spectroscopic assay and reverse line blotting (data not shown). However, at lower amounts of HPV, this concordance broke down (Table 6). The mass spectroscopic assay analysis consistently detected one of the 13 pathogenic HPV types at amounts <about 40 aM where both DNA sequencing and the reverse line blotting method either failed to detect any of the 13 types of highly pathogenic HPV or detected another type of HPV (Table 6). We confirmed this result by degenerate DNA sequencing which showed either the HPV type seen by reverse line blotting or a different non-pathogenic type of HPV (the spectrum of HPV types detected by reverse line blotting and DNA sequencing only partially overlaps explaining why these two techniques can give different answers; however, both techniques will work for all 13 pathogenic types of HPV (except for HPV 52 which does not amplify well using the degenerate sequencing method)). Note that this result of low titers that cannot be appreciated by other, less sensitive methods, differs from the control blood samples (with no HPV present) or Pap negative samples (with no HPV present in the vast majority of samples (FIG. 3D)). This argues strongly for the significance of these previously unappreciated low titers of pathogenic HPV that likely represent the vanishing traces of an HPV infection that was significant previously, but is now dying out. This is consistent with the observation that most HPV infections are cleared after 6 months-2 years. Together, this argues for the importance of obtaining longitudinal titers that may prevent a number of surgical procedures designed to extirpate lesions that would have been self-limited if it were possible to follow them longitudinally.

Mass spectroscopic assay, reverse line blotting and degenerate DNA sequencing on HC2 positive dysplasias. As with the pathologically abnormal cervical dysplasia samples, mass spectroscopic assay is more sensitive than reverse line blotting, degenerate DNA sequencing or HC2. There was excellent agreement between mass spectroscopic assay and the reverse line blotting method when there were at least about 50 copies of a pathogenic HPV type discerned, between mass spectroscopic assay and the degenerate DNA sequencing method when there were at least about 500 copies of a pathogenic HPV type discerned, and between HC2 and mass spectroscopic assay when there were at least about 5000 copies of a pathogenic HPV type discerned. Good agreement among all three techniques was observed in these cases among 98/125 HC2 positive samples analyzed by mass spectroscopic assay with more than about 5000 copies (Table 7). In the remaining 27/125 HC2 (+) cases with titers of pathogenic HPV <about 5000 copies, reverse line blotting and/or the degenerate DNA sequencing methods detected types of HPV other than the 13 highly pathogenic types detected by our mass spectroscopic assay (Table 8). These are likely to contain the significant fraction of dysplasias identified by HC2 that are false positives [2, 36].

The samples without HPV detected by DNA sequencing could consist of samples containing multiple types of HPV with similar concentrations that prevent obtaining DNA sequence from a single type of HPV, samples containing HPV types that diverge too much from the primers to amplify with the degenerate primers, and/or samples not containing sufficient HPV to yield amplification.

In 17 out of 18 cases where a cervical tumor had detectable HPV 16 DNA, we found that the serum and/or blood also had detectable HPV 16 DNA. Neither HPV 16 DNA nor HPV 18 DNA was detected in the serum and/or blood in any of the 3 cases where the tumor was negative for HPV 16 DNA and HPV 18 DNA. As we had observed in head/neck cancers, blood and serum results differed in many of the cervical cancer cases. Of the 18 samples that were positive in the tumor: 8 were positive in both serum and blood; 5 were positive in serum but not blood; 4 were positive in blood but not serum; and 1 was negative in both serum and blood.

Serum and blood samples from women with cervical dysplasia were then examined in accordance with the invention. None of these women had detectable HPV DNA in their serum or blood by TaqMan analyses with the degenerate probe. In contrast, mass spectroscopic assay analysis comprising some embodiments detected small amounts of HPV 16 DNA in serum and/or blood from a subset of individuals with cervical cancer (Table 9) or high grade dysplasia (Table 10). Four out of five cases with high grade cervical dysplasia were positive for HPV 16 DNA. HPV 16 DNA was also detected in serum from one individual with atypical squamous cells of uncertain significance and another subject with a diagnosis of vulvar intraepithelial neoplasia grade I and low grade cervical dysplasia. HPV 16 DNA was not observed in serum or blood of individuals who did not have active lesions. Further, the mass spectroscopic assay tests for HPV 16 DNA in serum or blood were always negative after successful removal of the previous high grade dysplasia or cancer in situ (cases 4, 5, 6, 15, 16, 17, 22, 24, 27, 44). Samples were not available before removal of the dysplasia in these cases. The one subject (case 1) who had high-grade cervical dysplasia without HPV DNA in serum or blood may have had an HPV type other than the HPV 16 or HPV 18 probes that I used at that time.

We then extended these findings to ensure that we could discern HPV types other than 16 or 18 in blood and/or serum of individuals with cervical dysplasias. As shown in Table 11, an appreciable fraction of the blood and/or serum samples was positive for HPV when the virus was present in a cervical dysplasia. This included several cases where the HPV types were other than 16 or 18. This underscores the potential clinical utility of monitoring blood and/or serum with highly sensitive techniques that can detect down to the level of individual molecules.

This illustrates the usefulness of the sensitive, specific and quantitative mass spectroscopic assay which comprises some embodiments of the invention, without limiting the scope of possible embodiments. The work demonstrates the important points that there is less HPV present in tumors than in dysplasia and that small amounts of pathogenic HPV are present in many tumors and dysplasias where either no HPV is present or other less pathogenic or non-pathogenic types of HPV may be present. In particular, the finding of pathogenic HPV in essentially all tumors, with the amounts decreasing continuously to zero, supports the hypothesis that there is a restricted set of pathogenic HPV types with the risk of another type of HPV to cause a tumor being very low. Finally, it is only by application of this sensitive technique that very low titers of HPV in blood and/or serum have been appreciated. Since this finding only occurs in people with dysplasias or cancers, and disappears upon removal of a dysplasia, this should represent an excellent way to detect these lesions and/or monitor the therapeutic effectiveness of techniques to remove these lesions.

Without limitation, in accordance with some embodiments of the invention, the technical development to achieve insight at this level of HPV includes the ability to detect non-abundant HPV sequences in a highly sensitive and specific manner. Thus, the invention comprises for the first time the ability and usefulness of accomplishing the sensitivity and specificity needed to diagnose individual HPV copies. Thus, the invention comprises systems, compositions, and/or methods to achieve this level of sensitivity and specificity and enables the detection of events that could not heretofore been appreciated, including the findings that cervical dysplasia is associated with detectable HPV in the blood and/or serum whereas normalcy is not associated with detectable HPV in the blood and/or serum. This avoids the use of inadequate TaqMan technology that yields frequent false positives [4] and false negatives (per our unpublished results) if serum HPV is to be detected.

A further advantage of the invention is that it is quantitative as well as sensitive and specific so that it allows for the determination of tumor burden, with larger or more aggressive tumors presumably being associated with higher HPV loads reflected in higher levels in cervical samples (after normalization for total DNA) [7], serum and/or blood. Further, there is likely clinical benefit from determining whether serum and/or blood are affected. For example, tumors undergoing hematogenous spread are likely associated with increased presence in blood whereas tumors undergoing increased lysis are likely associated with increased presence in serum. In sum, the mass spectroscopic assay technology was more sensitive at the same time that it provided complete specificity. This usefulness will extend both to members of populations at risk to develop these tumors, and to individuals in whom a previous tumor was diagnosed and are currently under observation.

Without limitation, preferred embodiments of the invention comprise systems methods, and compositions for detecting the cancers described herein in human patients by obtaining a biological sample from the patient, for example and without limitation, blood, serum, or urine samples and combinations of two or more thereof; detecting the number of copies of HPV genome in the samples according to techniques, including without limitation, those described herein, which have detection sensitivities below any currently approved tests, such as the Digene test, and calculating the number of copies of HPV genome in a known volume or other concentration measure of the sample, where the presence of HPV in the sample as low as the single copy level is indicative of cancer in the patient as taught by the invention. As one example only, and without limitation, while the Digene test does not permit detection below 5000 copies per serum sample, the present invention comprises detection capability down to single copy levels.

The invention comprises systems, compositions, and/or methods to accomplish detection at a very sensitive level that enabled observations described herein that were not previously possible. Thus, the invention comprised the finding that small amounts of HPV in body fluids are associated with cancer or dysplasia, which can then be eliminated by removal of the tumor or dysplasia. Indeed, the finding that cervical dysplasia yields detectable abnormalities in serum and blood, but that the serum and blood of normal controls is negative, is fully novel. In accordance with the invention, determination that blood is useful for both the head/neck and cervical tumors is also novel, as previous claims have utilized screens of blood by techniques that were not sensitive enough to prevent false negatives and/or whose specificity was not great enough to prevent false positives. Previous efforts to detect HPV in serum either utilized techniques that were not sufficiently sensitive and/or specific. Using the more sensitive and specific mass spectroscopic assay system of the invention, one can now detect HPV in a high fraction of schistosomiasis-associated bladder, cervical and head/neck tumors that are associated with finite and measurable serum HPV levels.

The invention comprises the finding that very sensitive and specific analyses of urine sediment, serum and/or blood can now be shown to be positive for HPV in cancer or dysplasia when using a sufficiently sensitive and specific method of analysis that detects down to the single copy level (notwithstanding the inescapable limits imposed by the uncertainty inherent from Poisson's distribution on very low numbers; this can be circumvented by performing multiple analyses). Further, HPV in serum and/or blood can be detected in cases of cervical dysplasia; the HPV then disappears when the dysplasia is extirpated. Taken together, the invention enables the determination of whether an HPV-associated cancer is present in at-risk subjects or in subjects undergoing treatment of dysplasia or cancer.

All references are incorporated in full by reference as though fully set forth herein.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements. It is intended that the following claims define the scope of the invention and that the systems, methods, and compositions within the scope of these claims and their equivalents be covered thereby.

TABLE 1A

Primers for first PCR amplification.
Priming should be at 60° C.

| PCR Product Length (nt) | FORWARD | PRIMER SEQUENCE | Primer Length | REVERSE | PRIMER SEQUENCE | Primer Length |
| --- | --- | --- | --- | --- | --- | --- |
| 102 | HPV18 | TGAAAAACGACGAITTCACAAC (SEQ ID NO. 1) | 22 | HPV18 | GTTTCTCIGCGTCGTTGGAG (SEQ ID NO. 23) | 20 |
| 94 | HPV45 | GTGCCAGAAACCAITGAACC (SEQ ID NO. 2) | 20 | HPV45 | ACACTGCCCICGGTACTGTC (SEQ ID NO. 24) | 20 |
| 100 | HPV39 | AGAACGGCCAIACAAATTGC (SEQ ID NO. 3) | 20 | HPV39 | TTGCTGTAGIGGTCGTCTGC (SEQ ID NO. 25) | 20 |
| 104 | HPV59 | TGTTTTGCAAIGGGGAACTG (SEQ ID NO. 4) | 20 | HPV59 | TTTCAGACICGCTGCATACG (SEQ ID NO. 26) | 20 |

TABLE 1A-continued

Primers for first PCR amplification.
Priming should be at 60° C.

| PCR Product Length (nt) | FORWARD | PRIMER SEQUENCE | Primer Length | REVERSE | PRIMER SEQUENCE | Primer Length |
|---|---|---|---|---|---|---|
| 83 | HPV56 | TTAACTCCGGIGGAAAAGC (SEQ ID NO. 5) | 19 | HPV56 | AAACAIGACCCGGTCCAAC (SEQ ID NO. 27) | 19 |
| 86 | HPV53 | GACCACGTACAITGCACCAG (SEQ ID NO. 6) | 20 | HPV53 | TGCCTTCTIGCAGAACACAC (SEQ ID NO. 28) | 20 |
| 92 | HPV51 | AAGGGTTAIGACCGAAAACG (SEQ ID NO. 7) | 20 | HPV51 | TTCGTGGTCITTCCCTCTTG (SEQ ID NO. 29) | 20 |
| 104 | HPV31 | AAAGTGGTGAICCGAAAACG (SEQ ID NO. 8) | 20 | HPV31 | TGCAATTICCGAGGTCTTTC (SEQ ID NO. 30) | 20 |
| 102 | HPV35 | ACATGTCAAIAACCGCTGTG (SEQ ID NO. 9) | 20 | HPV35 | GGACATACICCGACCTGTCC (SEQ ID NO. 31) | 20 |
| 84 | HPV33 | GGAAAAACCICGAACATTGC (SEQ ID NO. 10) | 20 | HPV33 | TTGCATTCCICGCACTGTAG (SEQ ID NO. 32) | 20 |
| 87 | HPV58 | AGGAGAAICCACGGACATTG (SEQ ID NO. 11) | 20 | HPV58 | TTTTGCATTCIACGCATTTC (SEQ ID NO. 33) | 20 |
| 80 | HPV52 | GAGGATCCIGCAACACGAC (SEQ ID NO. 12) | 19 | HPV52 | TGCAGCCTIATTTCATGCAC (SEQ ID NO. 34) | 20 |
| 104 | HPV73 | TCCACTGGAIAAGCAAAAGC (SEQ ID NO. 13) | 20 | HPV73 | CAGTTGCAGAIGGTCTCCAG (SEQ ID NO. 35) | 20 |
| 104 | HPV26 | AGAACGICCCAGAACGCTAC (SEQ ID NO. 14) | 20 | HPV26 | CAGCCCATIGTAAGGTTTCC (SEQ ID NO. 36) | 20 |
| 86 | HPV66 | CGGAGGAAIAACAATTGCAC (SEQ ID NO. 15) | 20 | HPV66 | CCAACACIGCAAACATGACC (SEQ ID NO. 37) | 20 |
| 84 | HPV68 | AATGGCGCIATTTCACAACC (SEQ ID NO. 16) | 20 | HPV68 | ACGTCAIGCAATGTGGTGTC (SEQ ID NO. 38) | 20 |
| 110 | HPV16 | TGCACAGAGCIGCAAACAAC (SEQ ID NO. 17) | 20 | HPV16 | ATGCATAAAICCCGAAAAGC (SEQ ID NO. 39) | 20 |
| 85 | HPV82 | TGCAGTCCCGIGCTATTACC (SEQ ID NO. 18) | 20 | HPV82 | TCCCAAAAIACAAGGCCATC (SEQ ID NO. 40) | 20 |
| 104 | HPV23 intron | TGGCTGTGCITATGCTTCTG (SEQ ID NO. 19) | 20 | HPV23 intron | TTTGGCCTAIAGGTCGTTGC (SEQ ID NO. 41) | 20 |
| 108 | ERB | CTAGCGAATGITTGTGTTGTC (SEQ ID NO. 20) | 21 | ERB | CCTCAGAGGIGGTACATGAG (SEQ ID NO. 42) | 20 |
| 108 | chlamydia | GTTCGGATTGIAGTCTGCAAC (SEQ ID NO. 21) | 21 | chlam | CGGGCGGIGTGTACAAGG (SEQ ID NO. 43) | 18 |
| 103 | neisseria | GCTAACGCGIGAAATTGACC (SEQ ID NO. 22) | 20 | neiss | GAATTAATCCICATCATCCACC (SEQ ID NO. 44) | 22 |

TABLE 1B

MassEXTENSION Primers
(Note: Mass has been corrected for deoxyinosine substitution)
Amplification Primers (all amplification-PCR primers are normalized to a calculated Tm of 58° C.)

| | SBE extension should be at 58° C. | | length w/out mods | target SBE | modifier mol wt | | molecular weight (daltons) | difference to next peak | ID (u = unextended, t = target gene, c = internal competitor) |
|---|---|---|---|---|---|---|---|---|---|
| 1 | HPV18* CCGAGCICGACAGGAAC | (SEQ ID NO. 45) | 17 | G | | 1 | 5199 | 289 | 18u |
| 2 | HPV45 /5AmMCI2/AGACACCITAAGGACAAAC | (SEQ ID NO. 46) | 19 | G | 264 | 2 | 5489 | 40 | 18c |
| 3 | HPV39 /5dSp/TTGCAGGACAITACAATAGC | (SEQ ID NO. 47) | 20 | C | 180 | 3 | 5529 | 39 | 18t |
| 4 | HPV59 /5AmMCI2/GGAACIGCAAGAAAGAGAG | (SEQ ID NO. 48) | 19 | G | 264 | 4 | 5568 | 89 | 31u |
| 5 | HPV56 /5AmMCI2/GGAAAGCAAITGCATTGTGACA | (SEQ ID NO. 49) | 22 | G | 264 | 5 | 5657 | 159 | 35u |
| 6 | HPV53 /5SpC3/CATTGCTGGAGCIGCAACTTG | (SEQ ID NO. 50) | 21 | G | 138 | 6 | 5816 | 41 | 16u |
| 7 | HPV51 /5dSp/GGTGCATAIAAAAGTGCAGTG | (SEQ ID NO. 51) | 21 | G | 180 | 7 | 5857 | 40 | 31t |
| 8 | HPV31 /5Phos/GTGCAAACCIACAGACGC | (SEQ ID NO. 52) | 18 | C | 80 | 8 | 5897 | 49 | 31c |
| 9 | HPV35 /5SpC3/CCATAACAICGGTGGACG | (SEQ ID NO. 53) | 18 | G | 138 | 9 | 5946 | 40 | 35c |
| 10 | HPV33 /5Phos/GAACATIGCATGATTTGTGC | (SEQ ID NO. 54) | 20 | C | 80 | 10 | 5986 | 87 | 35t |
| 11 | HPV58 CATTGCATGAITTGTGTCAGG | (SEQ ID NO. 55) | 21 | C | | 11 | 6073 | 32 | 45u |
| 12 | HPV52 /5AmMC6T/TGTGTGAGGIGCTGGAAGAATC | (SEQ ID NO. 56) | 22 | G | 458 | 12 | 6105 | 40 | 16c |
| 13 | HPV73 /5AmMC6T/GAAAAAAAACGGITTCATCAAATAG | (SEQ ID NO. 57) | 25 | C | 458 | 13 | 6145 | 73 | 16t |
| 14 | HPV26 /5SpI8/AGCTATGIGAAAGCTTGAATA | (SEQ ID NO. 58) | 21 | C | 344 | 14 | 6218 | 19 | 59u |
| 15 | HPV66 /5AmMC6T/AGGAAAAACAAITGCACTGTGAA | (SEQ ID NO. 59) | 23 | C | 458 | 15 | 6237 | 78 | 33u |
| 16 | HPV68 /5Phos/GCGCTATTCACAACCCTGAG | (SEQ ID NO. 60) | 21 | G | 80 | 16 | 6315 | 47 | 39u |
| 17 | HPV16 AAGCAACAGITACTGCGAC | (SEQ ID NO. 61) | 19 | G | | 17 | 6362 | 40 | 45c |
| 18 | HPV82 /5SpC3/CCGTGCTATIACCTGCCAAAAG | (SEQ ID NO. 62) | 22 | G | 138 | 18 | 6402 | 54 | 45t |
| 19 | HPV23 /5AmMC6T/CAATTTGAAAITCAACAATTTTAT | (SEQ ID NO. 63) | 24 | C | 458 | 19 | 6456 | 21 | 68u |
| 20 | intron ERB GCGCAATTCAITACCTCATTTAA | (SEQ ID NO. 64) | 23 | C | | 20 | 6477 | 30 | 58u |
| 21 | chlam /5Phos/ATGAAGTCGGAAITGCTAGTAAT | (SEQ ID NO. 65) | 23 | G | 80 | 21 | 6507 | 19 | 59c |
| 22 | neiss CGCAAGATTAAAACICAAAGGAATT | (SEQ ID NO. 66) | 25 | G | | 22 | 6526 | 21 | 33t |
| | | | | | | 23 | 6547 | 19 | 59t |
| | | | | | | 24 | 6566 | 19 | 33c |
| | | | | | | 25 | 6585 | 19 | 53u |
| | | | | | | 26 | 6604 | 40 | 39t |
| | | | | | | 27 | 6644 | 80 | 39c |
| | | | | | | 28 | 6724 | 21 | 51u |
| | | | | | | 29 | 6745 | 21 | 68c |
| | | | | | | 30 | 6766 | 19 | 58t |
| | | | | | | 31 | 6785 | 21 | 68t |
| | | | | | | 32 | 6806 | 21 | 58c |

TABLE 1B-continued

MassEXTENSION Primers
(Note: Mass has been corrected for deoxyinosine substitution)
Amplification Primers (all amplification-PCR primers are normalized to a calculated Tm of 58° C.)

| SBE extension should be at 58° C. | length w/out mods | target SBE | modifier mol wt | molecular weight (daltons) | difference to next peak | ID (u = unextended, t = target gene, c = internal competitor) |
|---|---|---|---|---|---|---|
| | | | 33 | 6827 | 20 | 82u |
| | | | 34 | 6847 | 27 | 26u |
| | | | 35 | 6874 | 40 | 53c |
| | | | 36 | 6914 | 53 | 53t |
| | | | 37 | 6968 | 46 | intron-u |
| | | | 38 | 7013 | 40 | 51c |
| | | | 39 | 7054 | 28 | 51t |
| | | | 40 | 7081 | 35 | 56u |
| | | | 41 | 7117 | 20 | 82c |
| | | | 42 | 7136 | 20 | 26t |
| | | | 43 | 7157 | 20 | 82t |
| | | | 44 | 7176 | 40 | 26c |
| | | | 45 | 7217 | 40 | chlam-u |
| | | | 46 | 7257 | 40 | intron-t |
| | | | 47 | 7297 | 42 | intron-c |
| | | | 48 | 7338 | 32 | 52u |
| | | | 49 | 7371 | 40 | 56c |
| | | | 50 | 7411 | 95 | 56t |
| | | | 51 | 7506 | 40 | chlam-c |
| | | | 52 | 7546 | 36 | chlam-t |
| | | | 53 | 7582 | 46 | 66u |
| | | | 54 | 7628 | 40 | 52c |
| | | | 55 | 7668 | 33 | 52t |
| | | | 56 | 7701 | 76 | neiss-u |
| | | | 57 | 7777 | 94 | 23u |
| | | | 58 | 7871 | 40 | 66t |
| | | | 59 | 7911 | 79 | 66c |
| | | | 60 | 7990 | 40 | neiss-c |
| | | | 61 | 8030 | 36 | neiss-t |
| | | | 62 | 8066 | 40 | 23t |
| | | | 63 | 8106 | 77 | 23c |

TABLE 1B-continued

MassEXTENSION Primers
(Note: Mass has been corrected for deoxyinosine substitution)
Amplification Primers (all amplification-PCR primers are normalized to a calculated Tm of 58° C.)

| SBE extension should be at 58° C. | length w/out mods | target get SBE | modi- fier mol wt | molecular weight (daltons) | difference to next peak | ID (u = unextended, t = target gene, c = internal competitor) |
|---|---|---|---|---|---|---|
| | | | | 8183 | 289 | 73u |
| | | | | 8472 | 40 | 73t |
| | | | | 8512 | | 73c |

*HPV18, Inosine replaces "A", not "T"

TABLE 1C

| | Competitor sequences (SBE position has been changed) | |
|---|---|---|
| HPV18 | GTTTCTCTGCGTCGTTGGAGTGGTTCCTGTCGTGCTCGGTTGCAGCACGAATGGCACTGGCCTCTATAGTGCC CAGCTATGTTGTGAAATCGTCGTTTTTCA | (SEQ ID NO. 67) |
| HPV45 | ACACTGCCCTCGGTACTGTCCAGCTATGCTGTGAAATCTTGGTTTGTCCTTAAGGTGTCTACGTTTTTCTGCT GGGTTCAATGGTTTCTGGCAC | (SEQ ID NO. 68) |
| HPV39 | TTGCTGTAGTGGTCGTCTGCAATAGACACACGCTATTGTAATGTCCTGCAAGGTGGTGTCCAGCGTTGTGCAC AGGTCTGGCAATTTGTATGGCCGTTCT | (SEQ ID NO. 69) |
| HPV59 | TTTCAGACACGCTGCATACGGTGTACAGTCTCTATACACTATAAATAAGTCATTAAAAGCAAATTCAAATAGC TCTCTTTCTTGCAGTTCCCCTTTGCAAAACA | (SEQ ID NO. 70) |
| HPV56 | AAACATGACCCGGTCCAACCATGTGCTATTAGATGAAATCGTCTTTTTGTGTCACAATGCAATTGCTTTTCCT CCGGAGTTAA | (SEQ ID NO. 71) |
| HPV53 | TGCCTTCTTGCAGAACACACAGGCAAGTTGCAGCTCCAGCAATGGTTTATTCACAACTTCACATAGCTGGTGC AATGTACGTGGTC | (SEQ ID NO. 72) |
| HPV51 | TTCGTGGTCTTTCCCTCTTGTCTTCGAACATGGTGTTCTTCTATACTTTTAGCACTGCACTTTTATATGCACC GTTTTCGGTCATAACCCTT | (SEQ ID NO. 73) |
| HPV31 | TGCAATTTCCGAGGTCTTTCTGCAGGATTTTTGAACATCGCGTCTGTAGGTTTGCACAAAATACTATGTGCTT TATATACCAACCGTTTTCGGTTCACCACTTT | (SEQ ID NO. 74) |
| HPV35 | GGACATACACCGACCTGTCCAGCGTCCACCGATGTTATGGAATCGTTTTTTTTCTTCTAAATGTCTTTGCTTT TCAACTGGACACAGCGGTTTTTGACATGT | (SEQ ID NO. 75) |
| HPV33 | TTGCATTCCACGCACTGTAGTTCAATGTTGTGTATAGTTGTCTCCAATGCTTCGCACAAATCATGCAATGTTC GTGGTTTTTCC | (SEQ ID NO. 76) |
| HPV58 | TTTTGCATTCAACGCATTTCAATTCGATTTCATGCACAGATGTCTCCAACCCCTGACACAAATCATGCAATGT CCGTGGTTTCTCCT | (SEQ ID NO. 77) |
| HPV52 | TGCAGCCTTATTTCATGCACGGATTCTTCCAGCACCTCACACAATTCGTGCAGGGTCCGGGGTCGTGTTGCTG GATCCTC | (SEQ ID NO. 78) |
| HPV73 | CAGTTGCAGATGGTCTCCAGCACCGTGTACAGCGTCCGGTCCACTGTTCTCCTATTTGATGAAACCGTTTTTT TTCATCTACATGCTTTTGCTTTTCCAGTGGA | (SEQ IN NO. 79) |
| HPV26 | CAGCCCATTGTAAGGTTTCCTTGCAATATACACACTGTACCTGCAAATTTTGCAAAGTACTATTCAAGCTTTC ACATAGCTCATGTAGCGTTCTGGGTCGTTCT | (SEQ ID NO. 80) |
| HPV66 | CCAACACTGCAAACATGACCCGGTCCATGCATATGCTATATAATGAAATCGTCTTTTATCTTCACAGTGCAAT TGTTTTTCCTCCG | (SEQ ID NO. 81) |
| HPV68 | ACGTCATGCAATGTGGTGTCCAATGTCCTGCACAGGTCTGGCAATTTGTATGGCCGTTGCTCAGGGTTGTGAA ATAGCGCCATT | (SEQ ID NO. 82) |
| HPV16 | ATGCATAAATCCCGAAAAGCAAAGTCATATACCTCAGGTCGCAGTAACTGTTGCTTGCAGTACACACATTCTA ATATTATATCATGTATAGTTGTTTGCAGCTCTGTGCA | (SEQ ID NO. 83) |

TABLE 1C-continued

Competitor sequences (SBE position has been changed)

| | | |
|---|---|---|
| HPV82 | TCCCAAAATACAAGGCCATCATAAGGATCCTTTTTAGGGGCAGGGGCGGAAGGACGCTTTTGGCAGGTAATAG<br>CACGGGACTGCA | (SEQ IN NO. 84) |
| HPV23 | TTTGGCCTATAGGTCGTTGCTCCTCCTGCTCAATTTCACGACCATACACAGTTAGCTCATAAAATTGTTGAAT<br>TTCAAATTGAGCAGAAGCATAAGCACAGCCA | (SEQ ID NO. 85) |
| intron erbB-2 | CCTCAGAGGAGGTACATGAGACTTAAATGAGGTAATGAATTGCGCAGCCATCTGTAAACATGACGAGGCTTTG<br>TAAACAGAACTGGGACAACACAAAACATTCGCTAG | (SEQ ID NO. 86) |
| chlamydia | CGGGCGGTGTGTACAAGGCCCGGGAACGTATTCACGGCGTTATGGCTGACACGCGATTACTAGCAATTCCGAC<br>TTCATGTAGTCGAGTTGCAGACTACAATCCGAAC | (SEQ ID NO. 87) |
| Neisseria | GAATTAATCCACATCATCCACCGCTTGTGCGGGTCCCCGTGAATTCCTTTGAGTTTTAATCTTGCGACCGTAC<br>TCCCCAGGCGGTCAATTTCACGCGTTAGC | (SEQ ID NO. 88) |

TABLE 1D

Spacer designations affixed to 5' end of extension primer

| Modifications | daltons | designation (Integrated DNA Technologies) |
|---|---|---|
| Phosphorylation | 80 | /5Phos/ |
| C3 spacer | 138 | /5SpC3/ |
| D spacer | 180 | /5dSp/ |
| Amino Modifier C12 | 264 | /5AmMC12/ |
| Spacer 18 | 344 | /5Sp18/ |
| Amino Modifier C6 dT | 458 | /5AmMC6T/ |

TABLE 2

Primers used for mass spectroscopic PCR assay using 13 HPV types.

| HPV type | FORWARD PRIMER SEQUENCE | REVERSE PRIMER SEQUENCE | MassEXTENSION Primers |
|---|---|---|---|
| HPV16 | ACGTTGGATGACTGCAATGTTTCAGGACCC<br>(SEQ ID NO. 89) | ACGTTGGATGTAGTTGTTTGCAGCTCTGTG<br>(SEQ ID NO. 90) | GAGCGACCCAGAAAGTTAC<br>(SEQ ID NO. 91) |
| HPV18 | ACGTTGGATGATAGCTGGGCACTATAGAGG<br>(SEQ ID NO. 92) | ACGTTGGATGTGTGTTTCTCTGCGTCGTTG<br>(SEQ ID NO. 93) | GCCATTCGTGCTGCAAC<br>(SEQ ID NO. 94) |
| HPV31 | ACGTTGGATGCAGGATTTTTGAACATGGCG<br>(SEQ ID NO. 95) | ACGTTGGATGTGGTGAACCGAAAACGGTTG<br>(SEQ ID NO. 96) | ATGGCGTCTGTAGGTTT<br>(SEQ ID NO. 97) |
| HPV33 | ACGTTGGATGCACAGTGCAGTTTCTCTACG<br>(SEQ ID NO. 98) | ACGTTGGATGCGATTTCATAATATTTCGGG<br>(SEQ ID NO. 99) | ACACGCCGCACAGCGCCCT<br>(SEQ ID NO. 100) |
| HPV35 | ACGTTGGATGTTCCAACAGGACATACACCG<br>(SEQ ID NO. 101) | ACGTTGGATGCGCTGTGTCCAGTTGAAAAG<br>(SEQ ID NO. 102) | ACCTGTCCACCGTCCAC<br>(SEQ ID NO. 103) |
| HPV39 | ACGTTGGATGGCCATACAAATTGCCAGACC<br>(SEQ ID NO. 104) | ACGTTGGATGTCGTCTGCAATAGACACAGG<br>(SEQ ID NO. 105) | TTGCCAGACCTGTGCACAAC<br>(SEQ ID NO. 106) |
| HPV45 | ACGTTGGATGCTGTGCACAAATCTGGTAGC<br>(SEQ ID NO. 107) | ACGTTGGATGAAGTGCATTACAGGATGGCG<br>(SEQ ID NO. 108) | AAATCTGGTAGCTTGTAGGGTCGTT<br>(SEQ ID NO. 109 |
| HPV51 | ACGTTGGATGGGTTATGACCGAAAACGGTG<br>(SEQ ID NO. 110) | ACGTTGGATGGTCTTTCCCTCTTGTCTTCG<br>(SEQ ID NO. 111) | CGGTGCATATAAAAGTGCAGTG<br>(SEQ ID NO. 112) |
| HPV52 | ACGTTGGATGATTGTGTGAGGTGCTGGAAG<br>(SEQ ID NO. 113) | ACGTTGGATGACCTCTCTTCGTTGTAGCTC<br>(SEQ ID NO. 114) | GTGCTGGAAGAATCGGTG<br>(SEQ ID NO. 115) |
| HPV56 | ACGTTGGATGCAAACATGACCCGGTCCAAC<br>(SEQ ID NO. 116) | ACGTTGGATGGTTAACTCCGGAGGAAAAGC<br>(SEQ ID NO. 117) | CAACCATGTGCTATTAGATGAAAT<br>(SEQ ID NO. 118) |
| HPV58 | ACGTTGGATGTGATTTGTGTCAGGCGTTGG<br>(SEQ ID NO. 119) | ACGTTGGATGTACCTCAGATCGCTGCAAAG<br>(SEQ ID NO. 120) | GTGTCAGGCGTTGGAGACAT<br>(SEQ ID NO. 121) |
| HPV59 | ACGTTGGATGGCAGTTCCCCTTTGCAAAAC<br>(SEQ ID NO. 122) | ACGTTGGATGCTGCCTGATTTGAGCACAAC<br>(SEQ ID NO. 123) | TTGCAAAACACACAATTGATG<br>(SEQ ID NO. 124) |
| HPV68 | ACGTTGGATGACCCCGTCCCTATATACTAC<br>(SEQ ID NO. 125) | ACGTTGGATGTGCAGAAGGCAACTACAACG<br>(SEQ ID NO. 126) | CCCTATATACTACATTTAAGTCA<br>(SEQ ID NO. 127) |

TABLE 2-continued

Primers used for mass spectroscopic PCR assay using 13 HPV types.

```
The competitor used for each HPV type is:
HPV16-Competitor
TAGTTGTTTGCAGCTCTGTGCATAACTGTCGTAACTTTCTGGGTCGCTCCTGTGGGTCCTGAAACATTGCAGT
(SEQ ID NO. 142)

HPV18-Competitor
TGTGTTTCTCTGCGTCGTTGGAGTCGTTCCTGTCGTGCTCCGTTGCAGCACGAATGGCACTGGCCTCTATAGTGCCCAGCTAT
(SEQ ID NO. 143)

HPV31-Competitor
CAGGATTTTTGAACATGGCGTCTGTAGGTTTCCACAAAATACTATGTGCTTTATATACCAACCGTTTTCGGTTCACCA
(SEQ ID NO. 144)

HPV33-Competitor
TCACAGTGCAGTTTCTCTACGTCGGGACCTCCAACACGCCGCACAGCGCCCTCCCCAACGACCCGAAATATTATGAAATCG
(SEQ ID NO. 145)

HPV35-Competitor
TTCCAACAGGACATACACCGACCTGTCCACCGTCCACGGATGTTATGGAATCGTTTTTTTTCTTCTAAATGTCTTTGCTTTTCAACTGGACACAGCG
(SEQ ID NO. 146)

HPV39-Competitor
TCGTCTGCAATAGACACAGGCTATTGTAATGTCCTGCAAGGTGGTGTCCAGGGTTGTGCACAGGTCTGGCAATTTGTATGGC
(SEQ ID NO. 147)

HPV45-Competitor
CATGTATTACACTGCCCTCGGTACTGTCCACCTATGCTGTGAAATCTTCGTTTGTCCTTAAGGTGTCTACGTTTTTCTGCTGGG
(SEQ ID NO. 148)

HPV51-Competitor
GTCTTTCCCTCTTGTCTTCGAACATGGTGTTCTTCTATACTTTTAGCACTGCACTTTTATATGCACCGTTTTCGGTCATAACC
(SEQ ID NO. 149)

HPV52-Competitor
ACCTCTCTTCGTTGTAGCTCTTTTTTGCACTGCACACACTGCAGCCTTATTTCATCCACCGATTCTTCCAGCACCTCACACAAT
(SEQ ID NO. 150)

HPV56-Competitor
CAAACATGACCCGGTCCAACCATGTGCTATTAGATGAAATGGTCTTTTTCTGTCACAATGCAATTGCTTTTCCTCCGGAGTTAAC
(SEQ ID NO. 151)

HPV58-Competitor
TACCTCAGATCGCTGCAAAGTCTTTTTGCATTCAACGCATTTCAATTCGATTTCATGCACACATGTCTCCAACGCCTGACACAAATCA
(SEQ ID NO. 152)

HPV59-Competitor
GCAGTTCCCCTTTGCAAAACACACAATTGATGGGAATATCATGCAGAGGAATATTCAATGTTGTGCTCAAATCAGGCAG
(SEQ ID NO. 153)

HPV68-Competitor
ACCCCGTCCCTATATACTACATTTAAGTCAGCAAAGGCAAATTCATATACCTCTGTCCGTTGTAGTTGCCTTCTGCA
(SEQ ID NO. 154)
```

TABLE 3

Mass spectroscopic assay analysis of HPV 16 DNA in schistosomiasis-associated bladder cancers

| | Detection by fluorescent QPCR | | | | Detection by Mass spectroscopic assay | | |
|---|---|---|---|---|---|---|---|
| sample # | Tumor | Serum | Urine sediment | sample # | Tumor | Serum | Urine sediment |
| 134 | 8.9E−06 | 6.2E−05 | 8.8E−05 | 134 | >1 fM | 0.3 aM | 1.2 aM |
| 138 | 7.5E−05 | 8.6E−05 | negative | 138 | 10 aM | 4.1 aM | negative |
| 17 | Negative | 4.4E−06 | | 17 | 100 aM | negative | |
| 20 | Negative | 7.6E−06 | 3.0E−05 | 20 | 10 aM | 0.2 aM | 3.0 aM |
| 204 | 2.4E−06 | 7.5E−06 | 2.9E−03 | 204 | >1 fM | >10 aM | 2.9 aM |
| 216 | 2.6E−04 | 2.1E−05 | negative | 216 | >1 fM | 16 aM | negative |
| 242 | 8.4E−05 | 1.3E−05 | negative | 242 | 100 aM | >10 aM | >10 aM |
| 296 | 2.2E−05 | 7.6E−05 | negative | 296 | 10 aM | 4.0 aM | 0.5 aM |

TABLE 3-continued

Mass spectroscopic assay analysis of HPV 16 DNA in schistosomiasis-associated bladder cancers

| | Detection by fluorescent QPCR | | | | Detection by Mass spectroscopic assay | | |
|---|---|---|---|---|---|---|---|
| sample # | Tumor | Serum | Urine sediment | sample # | Tumor | Serum | Urine sediment |
| 323 | Negative | 7.2E−06 | negative | 323 | >1 fM | 2.2 aM | 0.5 aM |
| 358 | 2.4E−05 | negative | negative | 358 | >1 fM | 1.6 aM | 1.6 aM |
| 380 | Negative | 6.3E−06 | negative | 380 | 100 aM | 0.8 aM | negative |
| 385 | 3.9E−06 | 2.3E−06 | 2.1E−05 | 385 | 1 0 aM | 10.4 aM | negative |
| 388 | 2.2E−05 | negative | | 388 | >1 fM | 1.3 aM | negative |
| 40 | 7.5E−05 | 2.2E−05 | negative | 40 | 100 aM | 0.5 aM | negative |
| 44 | | 1.5E−05 | | 44 | 40 aM | 0.4 aM | 0.6 aM |
| 407 | 9.4E−05 | 4.0E−06 | | 407 | >1 fM | 5.7 aM | 1.8 aM |
| 414 | Negative | 2.0E−06 | | 414 | 100 aM | 69 aM | 5.8 aM |
| 417 | 4.8E−06 | 1.1E−07 | | 417 | 57 aM | 3.8 aM | |
| 424 | Negative | negative | | 424 | 1 fM | >10 aM | >10 aM |
| 427 | 3.5E−05 | 9.7E−06 | | 427 | >1 fM | 6.7 aM | |
| 466 | 9.9E−06 | 5.2E−06 | | 466 | 100 aM | 1.1 aM | 1.0 aM |
| 51 | 4.0E−04 | 1.3E−04 | negative | 51 | 100 aM | 2.1 aM | >10 aM |
| 64 | | 4.1E−04 | 4.0E−05 | 64 | 100 aM | 0.4 aM | >10 aM |
| 84 | 1.9E−06 | 4.8E−06 | negative | 84 | 100 aM | 1.0 aM | negative |
| 65 | 4.0E−04 | 8.5E−06 | negative | 65 | | >10 aM | >10 aM |
| 269 | | 1.1E−05 | negative | 269 | | >10 aM | negative |
| 382 | negative | negative | negative | 382 | | 0.8 aM | negative | aM = attomolar;
fM = femtomolar

TABLE 4

Mass spectroscopic assay analysis of HPV 16 DNA in head/neck tumors, blood and serum.

| Tumor | Amount | blood | amount | Serum | amount | Tumor location |
|---|---|---|---|---|---|---|
| T19 | >1 fM | B61 | negative | S2048x | 1 aM | Oropharynx |
| T3 | 2 aM | B57 | 1 aM | S47x | negative | Tongue |
| T30 | 40 aM | B134 | 1 aM | S2070x | 1 aM | Tongue |
| T5 | 1 aM | B160 | 1 aM | S2016x | negative | Tongue |
| T23 | 200 aM | | | | | Tongue |
| T10 | >1 fM | | | | | Tongue |
| T9 | 1 fM | B142 | 1 aM | S2040x | 100 aM | Tongue |
| T18 | 30 aM | | | | | Tongue |
| | | B140 | 10 aM | S2057x | 1 aM | Tongue |
| T15 | Negative | B18 | negative | S2100x | negative | Tongue |
| T1 | >1 fM | | | | | tonsil |
| T17 | 100 aM | | | S2078x | 1 aM | tonsil |
| T8 | 100 aM | | | | | tonsil |
| T27 | >1 fM | B141 | 1 aM | S2053x | negative | tonsil |
| T28 | Negative | | | | | tonsil |
| T2 | Negative | | | S2047x | negative | soft palate |
| T4 | 100 aM | B126 | 10 aM | S2056x | 1 aM | hypopharynx |
| T22 | Negative | B23 | negative | | | larynx |
| T13 | Negative | B76 | negative | S2028x | negative | larynx |
| T12 | Negative | B44 | negative | S46x | negative | larynx |
| T16 | Negative | | | | | larynx |
| T24 | Negative | | | S2045x | negative | larynx |
| T14 | Negative | B112 | negative | S2020x | negative | supraglottic |
| T11 | Negative | | | | | supraglottic |
| T6 | Negative | | | | | supraglottic |
| T7 | Negative | B125 | negative | | | supraglottic | aM = attomolar;
fM = femtomolar

TABLE 5

Tumors: HPV typing by mass spectroscopic analysis and degenerate DNA sequencing.

| Tumor | HPV Type by mass spectroscope | # viruses/haploid genome equivalent | HPV type by DNA sequencing |
|---|---|---|---|
| C10 | HPV16 | 4.5E−03 | HPV16 |
| C12 | HPV16 | 7.6E−03 | HPV16 |
| C14 | HPV18 | 2.3E−02 | HPV18 |
| C16 | HPV52 | 1.5E−02 | None |
| C18 | HPV18 | 1.2E−03 | None |
| C20 | HPV18 | 2.9E−02 | HPV18 |
| C22 | HPV35 | 5.5E−02 | HPV35 |
| C24 | HPV18 | 9.2E−03 | HPV18 |
| C26 | HPV16 | 4.4E−02 | HPV16 |
| C27 | HPV52 | 1.7E−02 | None |
| C28 | HPV16 | 1.2E−02 | HPV16 |
| C30 | HPV18 | 1.7E−02 | HPV18 |
| C32 | HPV16, 45 | 5.3E−05 | HPV16 |
| C33A | HPV52 | 2.4E−05 | None |
| C37 | HPV16 | 4.0E−02 | HPV16 |
| C37 | HPV16 | 1.5E−01 | HPV16 |
| C3a | HPV16 | 1.1E−01 | HPV16 |
| C4 II | HPV18 | 4.3E−02 | HPV18 |
| C41 | HPV68 | 2.3E−03 | None |
| C43 | HPV16 | 4.8E−02 | HPV16 |
| C49 | HPV16 | 1.8E−02 | HPV16 |
| C51 | HPV16 | 1.2E−01 | HPV16 |
| C53 | HPV31 | 7.8E−02 | HPV31 |
| C55 | HPV31 | 4.1E−05 | HPV73 |
| C57 | HPV16 | 3.1E−03 | HPV16 |
| C5T | HPV16 | 0.0E+00 | HPV16 |
| C6 | HPV45 | 7.0E−02 | HPV45 |
| C62 | HPV52, 16 | 6.1E−03, 2.3E−05 | None |
| C63 | HPV18 | 4.9E−02 | HPV18 |
| C64 | HPV16 | 5.7E−04 | HPV16 |
| C67 | HPV16 | 4.3E−01 | HPV16 |
| C73 | HPV18 | 8.2E−03 | None |
| C8 | None | 0.0E+00 | None |
| CS122T | HPV18 | 4.5E−02 | HPV18 |
| CS179T | HPV16 | 1.2E+00 | HPV16 |
| CS18T | HPV59, 16 | 8.1E−02, 3.6E−04 | HPV16 |

TABLE 5-continued

Tumors: HPV typing by mass spectroscopic analysis and degenerate DNA sequencing.

| | HPV Type by mass spectroscope | # viruses/haploid genome equivalent | HPV type by DNA sequencing |
|---|---|---|---|
| CS191T | HPV33 | 2.0E−02 | HPV18 |
| CS195T | HPV59 | 9.1E−03 | None |
| CS196T | HPV16 | 4.8E−01 | HPV16 |
| CS198T | HPV16 | 9.0E−04 | HPV68 |
| CS19T | HPV16 | | HPV16 |
| CS202T | HPV16 | 2.8E−02 | HPV16 |
| CS203T | HPV16 | 6.9E−01 | HPV16 |
| CS204T | HPV16 | 6.9E−01 | HPV16 |
| CS205T | HPV16, 33 | 1.7E−04, 2.0E−05 | HPV16 |
| CS208T | HPV18 | 4.8E−03 | HPV18 |
| CS210T | HPV16 | 3.5E−01 | HPV16 |
| CS211T | HPV18 | 3.0E−01 | HPV18 |
| CS213T | HPV35, 16 | 1.2E−02, 3.2E−05 | HPV35 |
| CS214T | HPV16 | 2.5E−03 | HPV16 |
| CS22T | HPV16 | 4.9E−03 | HPV16 |
| CS24T | HPV16 | 1.1E−01 | HPV16 |
| CS2T | HPV45 | 1.2E−02 | HPV45 |
| CS30T | HPV56 | 3.2E−02 | None |
| CS32T | HPV52, 16 | 5.4E−02, 1.5E−03 | HPV16 |
| CS36T | HPV16 | 4.6E−02 | HPV16 |
| CS43T | HPV16 | 8.1E−03 | HPV16 |
| CS45T | HPV16 | 3.3E−01 | HPV16 |
| CS46T | HPV16 | 9.5E−02 | HPV16 |

TABLE 5-continued

Tumors: HPV typing by mass spectroscopic analysis and degenerate DNA sequencing.

| | HPV Type by mass spectroscope | # viruses/haploid genome equivalent | HPV type by DNA sequencing |
|---|---|---|---|
| CS83T | HPV16 | 1.0E−01 | HPV16 |
| CS85T | HPV16 | 3.2E−01 | HPV16 |
| CS8T | HPV16 | 1.3E−03 | HPV16 |
| CS90T | HPV18, 16 | 8.4E−03, 3.5E−04 | HPV18 |
| CS91T | HPV18, 16 | 2.0E−01, 4.3E−05 | HPV18 |
| CS92T | HPV16 | 1.5E−01 | HPV16 |
| CS93T | HPV18 | 9.9E−01 | HPV18 |
| CS96T | HPV16 | 2.9E−02 | HPV16 |
| CS98T | HPV45 | 1.5E−02 | HPV45 |
| CS9T | HPV16 | 1.3E−04 | HPV16 |
| UMC-2T | HPV59 | 5.7E−03 | None |
| UM-C3T | HPV18 | 1.4E−01 | None |
| UMC-3T | HPV18 | 1.4E−01 | None |
| UMC-4T | HPV45 | 7.2E−02 | HPV45 |
| Control cell lines | | | |
| Caski | HPV16 | 8.1E−01 | HPV16 |
| SiHa | HPV16 | 6.3E−03 | HPV16 |
| Hela | HPV18 | 5.9E−02 | HPV18 |

TABLE 6

Pathologic dysplasias with low amounts of pathogenic HPV by mass spectroscopic assay.

| Sample | HPV type by mass spectroscope | HPV amount by mass spectroscope | HPV type by sequencing | HPV type by reverse line blot | Pathology |
|---|---|---|---|---|---|
| PO 033 | HPV16, HPV35, HPV59 | all ~1 aM | none | No HPV | CIN I |
| PO 044 | HPV39, 51, 16 | 8 aM, ~1 aM, ~1 aM | none | No HPV | CIN II |
| PO 179 | HPV39, 51, 59, 68 | ~10 aM, ~10 aM, ~1 aM, ~10 aM | | No HPV | CIN I |
| PO 110 | HPV35, 58 | ~1 aM, ~1 aM | | HPV 73 | CIN I |
| PO 155 | HPV51 | ~1 aM | HPV81 | HPV 81 | CIN I |
| PO 185 | HPV35, 39, 58 | 43 aM, ~1 aM, ~1 aM | HPV35 | HPV 6 | CIN I |
| PO 223 | HPV52 | ~1 aM | none | HPV 84 | CIN I |
| PO 224 | HPV59 | ~1 aM | HPV81 | HPV 81 | CIN I |
| PO 231 | HPV35, 58 | ~1 aM, ~1 aM | HPV87 | HPV 42 | CIN I |
| PO 053 | HPV35, HPV 39 | ~5 aM, ~10 aM | HPV35 | HPV 53 | CIN I |
| PO 183 | HPV35, HPV56 | ~10 aM, 440 aM | HPV43 | HPV 53 & 83 | CIN I |
| PO 129 | HPV39, 58 | ~10 aM, 50 aM | HPV91 | HPV 55 | CIN I |
| PO 091 | HPV52 | ~10 aM | HPV66 | HPV 66 | CIN I |
| PO 130 | HPV39 | ~5 aM | HPV66 | HPV 66 | CIN I |
| PO 134 | HPV31 | 1.3 aM | none | HPV 66 | CIN I |
| PO 025 | HPV39, HPV51 | ~5 aM, ~1 aM | HPV73 | HPV 73 | CIN II |
| PO 150 | HPV35 | ~10 aM | HPV73 | HPV 73 | CIN I |
| PO 141 | HPV39, HPV68 | ~5 aM, ~5 aM | HPV43 | HPV 84 | CIN I |

TABLE 5-continued

Tumors: HPV typing by mass spectroscopic analysis and degenerate DNA sequencing.

| | HPV Type by mass spectroscope | # viruses/haploid genome equivalent | HPV type by DNA sequencing |
|---|---|---|---|
| CS47T | HPV16 | 3.2E−01 | |
| CS49T | HPV45, 16, 56 | 1.5E−02, 4.2E−03, 2.6E−04 | HPV16 |
| CS51T | HPV45, 16 | 1.6E−02, 1.7E−03 | None |
| CS59T | HPV16 | 2.5E−02 | HPV16 |
| CS59T | HPV31 | 3.7E−03 | HPV31 |
| CS63T | HPV31 | 7.5E−01 | HPV31 |
| CS6T | HPV33, 16 | 1.4E−02, 1.4E−03 | None |
| CS74T | HPV45 | 2.2E−02 | None |
| CS80T | HPV16 | 2.0E−02 | HPV16 |

TABLE 7

HPV types and copies (aM) present per haploid genome content of DNA in cervix ThinPrep samples.

| Samples positive by Digene method (HC II (+)) | HPV type(s) by mass spectroscope | Copies (aM)/ haploid genome |
|---|---|---|
| CDK01 | HPV16 | 3.40E+02 |
| CDK02 | HPV16 | 4.60E−03 |
| CDK03 | HPV39 | 2.70E+00 |
| CDK04 | Negative | 0.00E+00 |
| CDK05 | HPV16 | 1.30E−01 |
| CDK05 | HPV51 | 2.00E−03 |
| CDK06 | HPV39 | 7.40E−01 |
| CDK07 | HPV16 | 2.70E−02 |
| CDK08 | HPV16 | 2.90E+00 |

TABLE 7-continued

HPV types and copies (aM) present per haploid genome content of DNA in cervix ThinPrep samples.

| Samples positive by Digene method (HC II (+)) | HPV type(s) by mass spectroscope | Copies (aM)/ haploid genome |
|---|---|---|
| CDK08 | HPV58 | 4.10E−01 |
| CDK09 | HPV16 | 7.90E−03 |
| CDK10 | HPV31 | 4.00E−01 |
| CDK10 | HPV39 | 1.00E−04 |
| CDK11 | HPV33 | 8.80E−02 |
| CDK12 | HPV59 | 1.40E+00 |
| CDK12 | HPV18 | 1.20E+00 |
| CDK13 | HPV18 | 3.20E−01 |
| CDK14 | Negative | 0.00E+00 |
| CDK15 | Negative | 0.00E+00 |
| CDK16 | HPV33 | 1.10E+00 |
| CDK17 | HPV35 | 1.80E−01 |
| CDK18 | HPV31 | 1.30E−01 |
| CDK19 | HPV16 | 9.70E−01 |
| CDK19 | HPV31 | 1.40E−03 |
| CDK19 | HPV52 | 2.20E−04 |
| CDK20 | HPV31 | 1.40E+00 |
| CDK21 | HPV52 | 1.20E+00 |
| CDK22 | HPV45 | 7.20E−03 |
| CDK23 | HPV16 | 2.20E+00 |
| CDK24 | HPV39 | 2.20E−02 |
| CDK24 | HPV56 | 2.80E−04 |
| CDK25 | Negative | 0.00E+00 |
| CDK76 | HPV45 | 3.30E+01 |
| CDK77 | HPV16 | 3.30E+00 |
| CDK78 | HPV31 | 2.40E+00 |
| CDK78 | HPV16 | 2.10E+00 |
| CDK78 | HPV52 | 1.40E+00 |
| CDK78 | HPV45 | 2.30E−02 |
| CDK79 | HPV56 | 1.80E+03 |
| CDK80 | HPV52 | 6.70E+02 |
| CDK81 | HPV16 | 2.80E−01 |
| CDK82 | HPV56 | 2.20E+02 |
| CDK82 | HPV16 | 4.10E−01 |
| CDK83 | HPV16 | 6.20E+01 |
| CDK83 | HPV56 | 3.20E+00 |
| CDK84 | HPV31 | 5.60E+00 |
| CDK85 | Negative | 0.00E+00 |
| CDK86 | Negative | 0.00E+00 |
| CDK87 | HPV31 | 1.50E+01 |
| CDK88 | HPV16 | 6.80E−01 |
| CDK89 | HPV58 | 1.30E+01 |
| CDK90 | HPV31 | 2.30E+01 |
| CDK91 | HPV33 | 7.90E+00 |
| CDK91 | HPV68 | 1.20E−02 |
| CDK92 | HPV16 | 1.50E+00 |
| CDK92 | HPV33 | 1.70E−01 |
| CDK93 | HPV59 | 1.40E+01 |
| CDK93 | HPV16 | 4.70E−03 |
| CDK94 | HPV16 | 3.40E+01 |
| CDK95 | HPV18 | 2.80E+01 |
| CDK95 | HPV56 | 9.30E−01 |
| CDK96 | HPV31 | 3.20E+00 |
| CDK97 | HPV16 | 9.30E−03 |
| CDK98 | HPV39 | 2.20E+04 |
| CDK99 | HPV16 | 7.70E+00 |
| CDK100 | HPV18 | 9.90E+00 |
| CDK100 | HPV16 | 3.70E+00 |
| CDK100 | HPV52 | 2.30E+00 |
| CDK101 | HPV31 | 1.30E+00 |
| CDK101 | HPV59 | 5.00E−03 |
| CDK102 | HPV35 | 9.50E+00 |
| CDK102 | HPV39 | 3.90E−01 |
| CDK103 | HPV39 | 4.60E−03 |
| CDK104 | HPV52 | 1.30E−03 |
| CDK104 | HPV39 | 2.20E−05 |
| CDK105 | HPV39 | 3.20E−01 |
| CDK105 | HPV56 | 3.20E−01 |
| CDK105 | HPV16 | 3.20E−02 |
| CDK106 | HPV33 | 3.00E+00 |
| CDK107 | HPV56 | 1.40E−01 |
| CDK107 | HPV39 | 2.40E−03 |
| CDK108 | HPV59 | 2.20E−01 |
| CDK108 | HPV39 | 2.00E−03 |
| CDK108 | HPV56 | 2.00E−03 |
| CDK109 | HPV56 | 2.40E−01 |
| CDK109 | HPV16 | 1.80E−01 |
| CDK110 | HPV31 | 2.60E+01 |
| CDK110 | HPV18 | 2.60E−01 |
| CDK111 | HPV16 | 9.30E+00 |
| CDK112 | HPV56 | 3.20E+01 |
| CDK112 | HPV35 | 7.60E−03 |
| CDK113 | HPV51 | 6.50E−03 |
| CDK114 | HPV51 | 1.90E+02 |
| CDK114 | HPV35 | 3.90E+00 |
| CDK114 | HPV56 | 3.90E−01 |
| CDK114 | HPV39 | 6.50E−03 |
| CDK115 | HPV51 | 3.70E+01 |
| CDK115 | HPV39 | 1.40E−03 |
| CDK116 | HPV31 | 2.60E+00 |
| CDK117 | Negative | 0.00E+00 |
| CDK118 | HPV33 | 1.40E+02 |
| CDK119 | HPV51 | 2.90E+02 |
| CDK120 | HPV39 | 1.40E+00 |
| CDK121 | Negative | 0.00E+00 |
| CDK122 | HPV58 | 2.40E+01 |
| CDK123 | HPV58 | 2.60E+02 |
| CDK124 | HPV16 | 5.10E+00 |
| CDK124 | HPV52 | 7.50E−03 |
| CDK125 | HPV68 | 3.80E−03 |
| CDK126 | HPV31 | 9.20E−01 |
| CDK127 | HPV52 | 1.60E+01 |
| CDK127 | HPV16 | 2.80E−02 |
| CDK128 | HPV56 | 6.40E−03 |
| CDK129 | HPV16 | 2.90E+00 |
| CDK130 | HPV16 | 3.90E−01 |
| CDK130 | HPV35 | 8.50E−03 |
| CDK131 | HPV39 | 5.90E−03 |
| CDK132 | HPV16 | 2.00E+00 |
| CDK133 | HPV35 | 7.90E−03 |
| CDK134 | HPV51 | 1.20E−01 |
| CDK135 | HPV16 | 1.80E−03 |
| CDK136 | HPV56 | 4.30E+02 |
| CDK136 | HPV18 | 3.60E+01 |
| CDK136 | HPV16 | 5.00E−01 |
| CDK137 | HPV39 | 1.10E+00 |
| CDK138 | HPV59 | 3.50E+00 |
| CDK139 | HPV58 | 4.10E−01 |
| CDK140 | Negative | 0.00E+00 |
| CDK141 | HPV18 | 3.90E+01 |
| CDK142 | HPV52 | 1.40E+02 |
| CDK142 | HPV31 | 6.70E−01 |
| CDK143 | HPV56 | 2.50E−02 |
| CDK144 | HPV16 | 6.90E−02 |
| CDK145 | HPV51 | 7.20E−01 |
| CDK146 | HPV39 | 8.30E−03 |
| CDK147 | HPV16 | 1.40E+00 |
| CDK148 | HPV16 | 4.60E−01 |
| CDK149 | HPV31 | 9.00E+01 |
| CDK150 | HPV16 | 1.90E+01 |
| CDK176 | Negative | 0.00E+00 |
| CDK177 | HPV51 | 2.00E+00 |
| CDK178 | Negative | 0.00E+00 |
| CDK179 | HPV58 | 2.30E+00 |
| CDK180 | Negative | 0.00E+00 |
| CDK181 | HPV52 | 1.30E+02 |
| CDK181 | HPV18 | 1.50E+00 |
| CDK182 | HPV51 | 1.60E+03 |
| CDK183 | HPV39 | 1.80E+01 |
| CDK184 | HPV51 | 6.70E+00 |
| CDK185 | HPV56 | 9.10E+00 |
| CDK186 | HPV51 | 2.20E+01 |
| CDK187 | HPV16 | 6.10E+00 |
| CDK187 | HPV33 | 1.50E+00 |
| CDK188 | HPV16 | 1.10E+01 |
| CDK189 | HPV16 | 2.30E+01 |

TABLE 7-continued

HPV types and copies (aM) present per haploid genome content of DNA in cervix ThinPrep samples.

| Samples positive by Digene method (HC II (+)) | HPV type(s) by mass spectroscope | Copies (aM)/ haploid genome |
|---|---|---|
| CDK189 | HPV59 | 1.00E+01 |
| CDK190 | HPV16 | 4.60E+00 |
| CDK191 | HPV58 | 7.30E+02 |
| CDK192 | HPV51 | 7.50E+01 |
| CDK192 | HPV18 | 7.50E-02 |
| CDK193 | Negative | 0.00E+00 |
| CDK194 | HPV56 | 1.10E+03 |
| CDK195 | HPV56 | 8.00E-02 |
| CDK196 | HPV56 | 3.00E+00 |
| CDK197 | HPV59 | 3.60E+01 |
| CDK198 | HPV16 | 5.00E+02 |
| CDK198 | HPV59 | 1.80E+02 |
| CDK199 | HPV33 | 2.40E+01 |
| CDK199 | HPV45 | 1.90E+00 |
| CDK200 | HPV16 | 3.90E+01 |

TABLE 8

HC2 positive dysplasias with low amounts of pathogenic HPV by mass spectroscopic analysis

| Sample | HPV by MassARRAY | HPV copy #/ genome equivalent | DNA sequencing | reverse line blotting |
|---|---|---|---|---|
| CDK135 | HPV16 | 1.80E-03 | HPV67 | HPV67 |
| CDK97 | HPV16 | 9.30E-03 | HPV66 | HPV66 |
| CDK20 | HPV31 | 1.40E-03 | Negative | |
| CDK133 | HPV35 | 4.70E-03 | HPV32 | |
| CDK103 | HPV39 | 6.50E-03 | Negative | HPV40, 51 |
| CDK146 | HPV39 | 1.70E-02 | HPV66 | HPV66 |
| CDK22 | HPV45 | 7.20E-03 | HPV91 | |
| CDK113 | HPV51 | 6.50E-03 | Negative | |
| CDK104 | HPV52 | 1.30E-03 | Negative | |
| CDK80 | HPV52 | 6.70E-02 | HPV67 | |
| CDK128 | HPV56 | 1.30E-02 | HPV90 | |
| CDK143 | HPV56 | 6.50E-02 | Negative | |
| CDK195 | HPV56 | 8.00E-02 | HPV90 | |
| CDK125 | HPV68 | 1.10E-02 | Negative | HPV84, 89 |
| CDK14 | Negative | 0.00E+00 | HPV53 | HPV53 |
| CDK15 | Negative | 0.00E+00 | HPV53 | HPV53 |
| CDK117 | Negative | 0.00E+00 | HPV66 | HPV66 |
| CDK131 | Negative | 0.00E+00 | HPV30 | Negative |
| CDK140 | Negative | 0.00E+00 | HPV82 | HPV IS39 |
| CDK176 | Negative | 0.00E+00 | HPV26 | HPV82 |
| CDK178 | Negative | 0.00E+00 | HPV53 | HPV53 |
| CDK25 | Negative | 0.00E+00 | HPV54 | HPV54 |
| CDK85 | Negative | 0.00E+00 | HPV67 | HPV42, 52, 56, 89, XR |
| CDK86 | Negative | 0.00E+00 | HPV67 | HPV61 |
| CDK121 | Negative | 0.00E+00 | Negative | Negative |
| CDK180 | Negative | 0.00E+00 | Negative | HPV53 |
| CDK193 | Negative | 0.00E+00 | Negative | |

TABLE 9

Mass spectroscopic assay analysis of HPV 16 DNA in cervical cancer.

| sample # | tumor | peripheral blood | serum |
|---|---|---|---|
| 13 | >1 fM | 10 aM | 1 aM |
| 19 | >1 fM | 10 aM | negative |
| 38 | >1 fM | 10 aM | negative |
| 17 | >1 fM | 1 aM | 3 aM |
| 42 | >1 fM | negative | 60 aM |
| 12 | >1 fM | negative | negative |
| 37 | 900 aM | 2 aM | negative |
| 32 | 900 aM | negative | 5 aM |
| 39 | 800 aM | 16 aM | 10 aM |
| 16 | 500 aM | 1 aM | 1 aM |
| 3 | 400 aM | negative | 3 aM |
| 14 | 100 aM | 10 aM | 1 aM |
| 36 | 100 aM | 1 aM | 10 aM |
| 1 | 100 aM | 1 aM | 1 aM |
| 41 | 100 aM | 1 aM | negative |
| 18 | 100 aM | negative | 5 aM |
| 20 | 50 aM | 5 aM | 1 aM |
| 25 | 50 aM | 1 aM | 10 aM |
| 9 | negative | negative | negative |
| 26 | negative | negative | negative |
| 40 | negative | negative | negative |

TABLE 10

Mass spectroscopic assay analysis of HPV 16 DNA in cervical dysplasia.

| sample# | blood | serum | Diagnosis |
|---|---|---|---|
| 1 | negative | negative | High-grade cervical dysplasia |
| 4 | negative | negative | normal now; previous high-grade cervical dysplasia |
| 5 | negative | negative | normal now; previous high-grade cervical dysplasia |
| 6 | negative | negative | normal now; previous high-grade cervical dysplasia |
| 15 | negative | negative | normal now; previous high-grade cervical dysplasia |
| 16 | negative | negative | normal now; previous vaginal intraepithelial neoplasia grade 1 and cervical intraepithelial neoplasia grade 1 treated with 5-FU and surgery |
| 17 | negative | negative | normal now; previous vulvar intraepithelial neoplasia grade 3 treated with surgery |
| 22 | negative | negative | normal now; follow up for high grade cervical dysplasia previously treated by LEEP |
| 24 | negative | negative | normal now; previous high-grade cervical dysplasia |
| 27 | negative | negative | normal now; previous cervical intraepithelial neoplasia grade 1 I removed on colposcopy |
| 44 | negative | negative | normal now; s/p LEEP 10 days earlier for high-grade cervical dysplasia |
| 58 | negative | 36 aM | high-grade cervical dysplasia |
| 65 | negative | 41 aM | atypical squamous cells of uncertain significance |
| 55 | negative | 340 aM | vulvar intraepithelial neoplasia grade I + low grade cervical dysplasia |
| 60 | 180 aM | 43 aM | high-grade cervical dysplasia |
| 67 | >1000 aM | 130 aM | high-grade cervical dysplasia |
| 70 | 59 aM | 100 aM | high-grade cervical dysplasia |

TABLE 11

Presence of HPV in blood and/or serum for different HPV types present in dysplasia.

| HPV type in dysplasia | Fraction positive in blood and/or serum |
|---|---|
| HPV 16 | 12/24 |
| HPV 18 | 3/9 |
| HPV 31 | 1/1 |
| HPV 33 | 1/5 |
| HPV 35 | 0/1 |
| HPV 45 | 0/4 |
| HPV 52 | 1/1 |
| HPV 58 | 0/1 |
| HPV 59 | 0/1 |

REFERENCES

1. OBISO, R. AND A. LORINCZ, *DIGENE CORPORATION*. PHARMACOGENOMICS, 2004. 5(1): P. 129-32.
2. POLJAK, M., ET AL., *HYBRID CAPTURE II HPV TEST DETECTS AT LEAST 15 HUMAN PAPILLOMA VIRUS GENOTYPES NOT INCLUDED IN ITS CURRENT HIGH-RISK PROBE COCKTAIL*. J CLIN VIROL, 2002. 25 SUPPL 3: P. S89-97.
3. CAPONE, R. B., ET AL., *DETECTION AND QUANTITATION OF HUMAN PAPILLOMA VIRUS (HPV) DNA IN THE SERA OF PATIENTS WITH HPV-ASSOCIATED HEAD AND NECK SQUAMOUS CELL CARCINOMA*. CLIN CANCER RES, 2000.6(11): P. 4171-5.
4. YANG, H. J., ET AL., *QUANTIFICATION OF HUMAN PAPILLOMA VIRUS DNA IN THE PLASMA OF PATIENTS WITH CERVICAL CANCER*. INT J GYNECOL CANCER, 2004. 14(5): P. 903-10.
5. MUNOZ, N., ET AL., *EPIDEMIOLOGIC CLASSIFICATION OF HUMAN PAPILLOMA VIRUS TYPES ASSOCIATED WITH CERVICAL CANCER*. N ENGL J MED, 2003. 348(6): P. 518-27.
6. CHIN-HONG, P. V., ET AL., *AGE-RELATED PREVALENCE OF ANAL CANCER PRECURSORS IN HOMOSEXUAL MEN: THE EXPLORE STUDY*. J NATL CANCER INST, 2005. 97(12): P. 896-905.
7. MOBERG, M., l. GUSTAVSSON, AND U. GYLLENSTEN, *TYPE-SPECIFIC ASSOCIATIONS OF HUMAN PAPILLOMAVIRUS LOAD WITH RISK OF DEVELOPING CERVICAL CARCINOMA IN SITU*. INT J CANCER, 2004.112(5): P. 854-9.
8. DING, C. AND C. R. CANTOR, *A HIGH-THROUGHPUT GENE EXPRESSION ANALYSIS TECHNIQUE USING COMPETITIVE PCR AND MATRIX-ASSISTED LASER DESORPTION IONIZATION TIME-OF-FLIGHT MS*. PROC NATL ACAD SCI USA, 2003.100(6): P. 3059-64.
9. DING, C. AND C.R. CANTOR, *QUANTITATIVE ANALYSIS OF NUCLEIC ACIDS—THE LAST FEW YEARS OF PROGRESS*. J BIOCHEM MOL BIOL, 2004. 37(1): P. 1-10.
10. TANG, K., ET AL., *MINING DISEASE SUSCEPTIBILITY GENES THROUGH SNP ANALYSES AND EXPRESSION PROFILING USING MALDI-TOF MASS SPECTROMETRY*. J PROTEOME RES, 2004. 3(2): P. 218-27.
11. KHALED, H. M., ET AL., *HUMAN PAPILLOMA VIRUS INFECTION AND OVEREXPRESSION OF P53 PROTEIN IN BILHARZIAL BLADDER CANCER*. TUMORI, 2001. 87(4): P. 256-61.
12. GRAVITT, P. E., ET AL., *GENOTYPING OF 27 HUMAN PAPILLOMA VIRUS TYPES BY USING L1 CONSENSUS PCR PRODUCTS BY A SINGLE-HYBRIDIZATION, REVERSE LINE BLOT DETECTION METHOD*. J CLIN MICROBIOL, 1998. 36(10): P. 3020-7.
13. HEID C A, S. J., LIVAK K J, AND WILLIAMS P M., *REAL TIME QUANTITATIVE PCR*, IN *GENOME RESEARCH*. 1996. P. 986-994.
14. THOMPSON, G. H. AND A. ROMAN, *EXPRESSION OF HUMAN PAPILLOMA VIRUS TYPE 6 E1, E2, L1 AND L2 OPEN READING FRAMES IN ESCHERICHIA COLI*. GENE, 1987. 56(2-3): P. 289-95.
15. DE RODA HUSMAN, A. M., ET AL., *THE USE OF GENERAL PRIMERS GP5 AND GP6 ELONGATED AT THEIR 3' ENDS WITH ADJACENT HIGHLY CONSERVED SEQUENCES IMPROVES HUMAN PAPILLOMA VIRUS DETECTION BY PCR*. J GEN VIROL, 1995. 76 (PT 4): P. 1057-62.
16. NELSON, J. H., ET AL., *A NOVEL AND RAPID PCR-BASED METHOD FOR GENOTYPING HUMAN PAPILLOMAVIRUSES IN CLINICAL SAMPLES*. J CLIN MICROBIOL, 2000.38(2): P. 688-95.
17. STROUN, M., ET AL., *ISOLATION AND CHARACTERIZATION OF DNA FROM THE PLASMA OF CANCER PATIENTS*. EUR J CANCER CLIN ONCOL, 1987. 23(6): P. 707-12.
18. YANG, H., ET AL., *SENSITIVE DETECTION OF HUMAN PAPILLOMA VIRUS IN CERVICAL, HEAD/NECK, AND SCHISTOSOMIASIS-ASSOCIATED BLADDER MALIGNANCIES*. PROC NATL ACAD SCI USA, 2005.102(21): P.7683-8.
19. ELVIDGE, G. P., ET AL., *DEVELOPMENT AND EVALUATION OF REAL COMPETITIVE PCR FOR HIGH-THROUGHPUT QUANTITATIVE APPLICATIONS*. ANAL BIOCHEM, 2005. 339(2): P. 231-41.
20. SCHEFFNER, M., ET AL., *THE E6 ONCOPROTEIN ENCODED BY HUMAN PAPILLOMA VIRUS TYPES 16 AND 18 PROMOTES THE DEGRADATION OF P53*. CELL, 1990. 63(6): P. 1129-36.
21. HA, P. K., ET AL., *REAL-TIME QUANTITATIVE PCR DEMONSTRATES LOW PREVALENCE OF HUMAN PAPILLOMA VIRUS TYPE 16 IN PREMALIGNANT AND MALIGNANT LESIONS OF THE ORAL CAVITY*. CLIN CANCER RES, 2002. 8(5): P. 1203-9.
22. CHANG, J. Y., M. C. LIN, AND C. P. CHIANG, *HIGH-RISK HUMAN PAPILLOMA VIRUSES MAY HAVE AN IMPORTANT ROLE IN NON-ORAL HABITS-ASSOCIATED ORAL SQUAMOUS CELL CARCINOMAS IN TAIWAN*. AM J CLIN PATHOL, 2003. 120(6): P. 909-16.
23. NEVILLE, B. W. AND T. A. DAY, *ORAL CANCER AND PRECANCEROUS LESIONS*. CA CANCER J CLIN, 2002. 52(4): P.195-215.
24. HERRERO, R., ET AL., *HUMAN PAPILLOMA VIRUS AND ORAL CANCER: THE INTERNATIONAL AGENCY FOR RESEARCH ON CANCER MULTICENTER STUDY*. J NATL CANCER INST, 2003.95(23): P.1772-83.
25. MCKAIG, R. G., R. S. BARIC, AND A. F. OLSHAN, *HUMAN PAPILLOMAVIRUS AND HEAD AND NECK CANCER: EPIDEMIOLOGY AND MOLECULAR BIOLOGY*. HEAD NECK, 1998. 20(3): P. 250-65.
26. SCHWARTZ, S. R., ET AL., *HUMAN PAPILLOMA VIRUS INFECTION AND SURVIVAL IN ORAL SQUAMOUS CELL CANCER: A POPULATION-BASED STUDY*. OTOLARYNGOL HEAD NECK SURG, 2001. 125(1): P. 1-9.
27. KOCH, W. M., ET AL., *HEAD AND NECK CANCER IN NONSMOKERS: A DISTINCT CLINICAL AND MOLECULAR ENTITY*. LARYNGOSCOPE, 1999. 109 (10): P. 1544-51.

28. GILLISON, M. L., ET AL., *EVIDENCE FOR A CAUSAL ASSOCIATION BETWEEN HUMAN PAPILLOMA VIRUS AND A SUBSET OF HEAD AND NECK CANCERS*. J NATL CANCER INST, 2000. 92(9): P. 709-20.
29. SCHWARTZ, S. M., ET AL., *ORAL CANCER RISK IN RELATION TO SEXUAL HISTORY AND EVIDENCE OF HUMAN PAPILLOMA VIRUS INFECTION*. J NATL CANCER INST, 1998. 90(21): P. 1626-36.
30. SEYBOLT, G. F. AND G. N. PAPANICOLAU, [*EXFOLIATIVE CYTOLOGY: ITS VALUE IN THE DIAGNOSIS OF CANCER.*]. ARCH MED CUBA, 1953. 4(6): P. 579-86.
31. ROCK, C. L., ET AL., *PREVENTION OF CERVIX CANCER*. CRIT REV ONCOL HEMATOL, 2000. 33(3): P. 169-85.
32. BOSCH, F. X., ET AL., *PREVALENCE OF HUMAN PAPILLOMA VIRUS IN CERVICAL CANCER: A WORLDWIDE PERSPECTIVE. INTERNATIONAL BIOLOGICAL STUDY ON CERVICAL CANCER (IBSCC) STUDY GROUP*. J NATL CANCER INST, 1995. 87(11): P. 796-802.
33. JACOBS, M. V., ET AL., *GROUP-SPECIFIC DIFFERENTIATION BETWEEN HIGH-AND LOW-RISK HUMAN PAPILLOMA VIRUS GENOTYPES BY GENERAL PRIMER-MEDIATED PCR AND TWO COCKTAILS OF OLIGONUCLEOTIDE PROBES*. J CLIN MICROBIOL, 1995. 33(4): P. 901-5.
34. WALBOOMERS, J. M., ET AL., *HUMAN PAPILLOMAVIRUS IS A NECESSARY CAUSE OF INVASIVE CERVICAL CANCER WORLDWIDE*. J PATHOL, 1999. 189(1): P. 12-9.
35. VAN HAM, M. A., ET AL., *COMPARISON OF TWO COMMERCIAL ASSAYS FOR DETECTION OF HUMAN PAPILLOMA VIRUS (HPV) IN CERVICAL SCRAPE SPECIMENS: VALIDATION OF THE ROCHE AMPLICOR HPV TEST AS A MEANS TO SCREEN FOR HPV GENOTYPES ASSOCIATED WITH A HIGHER RISK OF CERVICAL DISORDERS*. J CLIN MICROBIOL, 2005. 43(6): P. 2662-7.
36. CASTLE, P. E., ET AL., *RESTRICTED CROSS-REACTIVITY OF HYBRID CAPTURE 2 WITH NONONCOGENIC HUMAN PAPILLOMAVIRUS TYPES*. CANCER EPIDEMIOL BIOMARKERS PREV, 2002. 11 (11): P. 1394-9.
37. NAM, J. M., S. I. STOEVA, AND C. A. MIRKIN, *BIO-BAR-CODE-BASED DNA DETECTION WITH PCR-LIKE SENSITIVITY*. J AM CHEM SOC, 2004. 126(19): P. 5932-3.
38. NAM, J. M., C. S. THAXTON, AND C. A. MIRKIN, *NANOPARTICLE-BASED BIO-BAR CODES FOR THE ULTRASENSITIVE DETECTION OF PROTEINS*. SCIENCE, 2003. 301(5641): P. 1884-6.

What is claimed is:

1. A method for detecting, identifying, and/or quantifying HPV DNA in a mammalian biological sample, comprising the steps of:
   extracting DNA from a mammalian biological sample;
   conducting a first amplification by PCR of at least a portion of the extracted DNA in the presence of at least one competitor sequence, said competitor sequence comprising a polynucleotide substantially homologous to a polynucleotide in a DNA sequence of a known HPV type, said competitor sequence having a nucleotide substitution not present in said HPV DNA sequence;
   conducting a second amplification by PCR in the presence of at least one extension primer for said known HPV type and at least two different dideoxynucleotides; and
   determining the level of any amplified extension primer for said known HPV type by mass spectrometry; wherein the first amplification comprises at least one matched set of forward and reverse primer sequences for a known HPV type substantially matching at least one competitor sequence and wherein at least one extension primer relates to the same known HPV type; wherein the first amplification comprises the extracted DNA in the presence of at least one competitor sequence comprising a polynucleotide substantially homologous to a polynucleotide in a DNA sequence of gene erbB-2, said competitor sequence having a nucleotide substitution not present in said gene erbB-2.

2. The method of claim 1, wherein the first amplification comprises at least one matched set of forward and reverse primer sequences relating to said known HPV type, each such sequence comprised of at least one inosine base.

3. The method of claim 1, wherein at least one extension primer is comprised of at least one inosine base.

4. The method of claim 1, wherein said determining step comprises detection of any amplified extension primer at a concentration below, or about, 200 attomolar.

5. The method of claim 1, wherein the first amplification comprises the presence of a plurality of competitor sequence types each comprising a polynucleotide substantially homologous to a polynucleotide in a DNA sequence of a different known HPV type, said competitor sequence type having a nucleotide substitution not present in said respective HPV DNA sequence and wherein the second amplification comprises the presence of a plurality of external primer types each for a different known HPV type.

6. The method of claim 5, wherein the plurality of known HPV types comprises two or more of HPV types 16, 18, 23, 26, 31, 33, 35, 39, 45, 51, 52, 53, 56, 58, 59, 66, 68, 73 and 82.

7. The method of claim 5, wherein the plurality of known HPV types comprises at least HPV types 16, 18, 23, 26, 31, 33, 35, 39, 45, 51, 52, 53, 56, 58, 59, 66, 68, 73 and 82.

8. A method for quantifying HPV DNA in a urine sample, comprising the steps of:
   extracting DNA from said urine sample;
   conducting a first amplification by PCR of at least a portion of the extracted DNA in the presence of at least one competitor sequence, said competitor sequence comprising a polynucleotide substantially homologous to a polynucleotide in a DNA sequence of a known HPV type, said competitor sequence having a nucleotide substitution not present in said HPV DNA sequence;
   conducting an extension reaction by PCR in the presence of at least one extension primer for said known HPV type and at least two different dideoxynucleotides; and
   determining the level of any amplified extension primer for said known HPV type by mass spectrometry.

9. The method of claim 8, wherein said known HPV type is selected from the group consisting of one or more of HPV types 16, 18, 23, 26, 31, 33, 35, 39, 45, 51, 52, 53, 56, 58, 59, 66, 68, 73 and 82.

10. The method of claim 8, wherein at least one extension primer is comprised of a spacer molecule affixed to the primer's 5' end, such spacer selected from the group consisting of phosphorylation, a C3 spacer, a D spacer, an amino modifier C12, a spacer 18, and an amino modifier C6 dT.

11. The method of claim 8, wherein said quantifying of said HPV DNA is used to identify a subject having or at risk for bladder cancer.

* * * * *